(12) United States Patent
Lee et al.

(10) Patent No.: US 6,448,407 B1
(45) Date of Patent: Sep. 10, 2002

(54) ATROPISOMERS OF ASYMMETRIC XANTHENE FLUORESCENT DYES AND METHODS OF DNA SEQUENCING AND FRAGMENT ANALYSIS

(75) Inventors: Linda G. Lee, Palo Alto; Meng C. Taing, San Mateo; Barnett B. Rosenblum, San Jose, all of CA (US)

(73) Assignee: PE Corporation (NY), Foster City, CA (US)

( * ) Notice: Subject to any disclaimer, the term of this patent is extended or adjusted under 35 U.S.C. 154(b) by 0 days.

(21) Appl. No.: 09/704,966

(22) Filed: Nov. 1, 2000

(51) Int. Cl.7 ...................... C07D 311/82; C07D 403/04
(52) U.S. Cl. ..................... 546/283.1; 549/223; 549/224
(58) Field of Search ............................... 549/223, 224; 546/283.1

(56) References Cited

PUBLICATIONS

Madge et al, Photochemistry and Photobiology, vol. 70, No. 5, Nov. 1999, pp. 737–744.*

* cited by examiner

*Primary Examiner*—Zinna Northington Davis
(74) *Attorney, Agent, or Firm*—Alex Andrus

(57) ABSTRACT

Substantially pure atropisomers of xanthene compounds are disclosed. A variety of molecular biology applications utilize atropisomeric xanthene fluorescent dyes as labels for substrates such as nucleotides, nucleosides, polynucleotides, polypeptides and carbohydrates. Methods include DNA sequencing, DNA fragment analysis, PCR, SNP analysis, oligonucleotide ligation, amplification, minisequencing, and primer extension.

57 Claims, 21 Drawing Sheets

24 R = OH
17 R = NHS

119　Racemic mixture　242

119　Substantially pure atropisomer　242

Phosphate-linker, energy-transfer terminator ddA 25

148　　　　　　　　　　　　　　　　　　　　　　　　205
Racemic mixture 148　　　　　　　　　　　　　　　　　　　　　　　　205
Substantially pure atropisomer Phosphate-linker, energy-transfer terminator ddA 25

148                                              242
Racemic mixture 148                                              242
Substantially pure atropisomer Sulfonate-linker, energy-transfer terminator ddA 24　　　　　　　　　　　　　　　　　　　　　　　　　　　99
Racemic mixture 24　　　　　　　　　　　　　　　　　　　　　　　　　　　99
Substantially pure atropisomer Energy-transfer terminator ddG

ATROPISOMERS OF ASYMMETRIC XANTHENE FLUORESCENT DYES AND METHODS OF DNA SEQUENCING AND FRAGMENT ANALYSIS

FIELD OF THE INVENTION

The invention relates to certain atropisomer forms of asymmetric xanthene fluorescent dyes and the field of nucleic acid sequencing and analysis with fluorescent dye-labelled reagents.

BACKGROUND OF THE INVENTION

Methods of analyzing fluorescent-labelled biomolecules after separating based on size- or charge are central to molecular biology. Examples of methods utilizing fluorescent-labelled nucleic acids include automated DNA sequencing, oligonucleotide probe methods, detection of polymerase-chain-reaction products, immunoassays, and the like. In the case of multi-color automated DNA sequencing, labelled nucleic acid fragments of varying size are separated by electrophoresis, typically in a single electrophoresis lane, channel, or capillary. Employing these methods, automated four-color Sanger-type DNA sequencing has enabled entire genome characterization at the molecular level.

Stereochemical purity is of importance in the field of pharmaceuticals, where 12 of the 20 most prescribed drugs exhibit chirality (U.S. Pat. No. 6,075,024). A case in point is provided by the L-form of the beta-adrenergic blocking agent, R(−) albuterol, which is known to be 100 times more potent than the D-enantiomer (U.S. Pat. No. 5,760,090). Furthermore, optical purity is important since certain isomers may actually be deleterious rather than simply inert.

Atropisomers are stereoisomeric conformations of a molecule whose interconversion is slow enough to allow separation and isolation under predetermined conditions (McGraw-Hill Dictionary of Chemical Terms, (1984), S. Parker, Ed., p. 36). The energy barrier to thermal racemization may be determined by the steric hindrance to free rotation of one or more bonds forming a chiral axis. Certain biaryl compounds exhibit atropisomerism where rotation around an intraannular bond lacking $C_2$ symmetry is restricted. The free energy barrier for enantiomerization is a measure of the stability of the intraannular bond with respect to rotation. Optical and thermal excitation can promote racemization, dependent on electronic and steric factors (Tetreau (1982) Nouv. Jour. de Chimie, 6:461–65).

Ortho-substituted biphenyl compounds may exhibit this type of conformational, rotational isomerism known as atropisomerism (Eliel, E. and Wilen, S. (1994) *Stereochemistry of Organic Compounds,* John Wiley & Sons, Inc., pp. 1142–55). Such biphenyls are enantiomeric, chiral atropisomers where the sp2-sp2 carbon-carbon, intraannular bond between the phenyl rings has a sufficiently high energy barrier to free rotation, and where substituents X≠Y and U≠V render the molecule asymmetric. The steric interaction of X—U, X—V, and/or Y—V, Y—U is large enough to make the planar conformation an energy maximum. Two nonplanar, axially chiral enantiomers, shown below, then exist as atropisomers when their interconversion is slow enough such that they can be isolated free of each other. By one definition, atropisomerism is defined to exist where the isomers have a half-life t½ of at least 1000 seconds, which is a free energy barrier of 22.3 kcal mol$^{-1}$ (93.3 kJ mol$^{-1}$) at 300K (Oki, M. (1983) "Recent Advances in Atropisomerism," Topics in Stereochemistry, 14:1). Bold lines and dashed lines in the figures shown below indicate those moieties, or portions of the molecule, which are sterically restricted due to a rotational energy barrier. Bolded moieties exist orthoganally above the plane and dashed moieties exist orthogonally below the plane of the rest of the molecule.

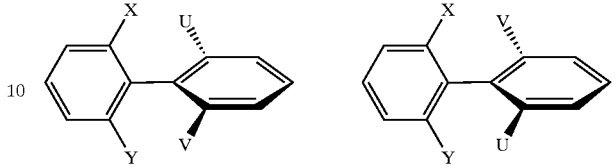

Xanthene dyes have important applications as detectable fluorescent labels of nucleic acids (U.S. Pat. Nos. 5,188,934; 5,654,442; 5,885,778; 6,096,723; 6,020,481; 5,863,727; 5,800996; 5,945,526; 5,847,162; 6,025,505; 6,008,379; 5,936,087; 6,015,719). Xanthene compounds containing an asymmetric biannular bond can exist in stable atropisomeric forms. Conjugates of atropisomeric xanthene compounds and chiral substrates, such as nucleotides, polynucleotides, polypeptides, and carbohydrates, form diastereomers. These diastereomeric conjugates can separate under certain conditions, such as electrophoresis, chromatography, and other methods. Separation of diastereomers can hinder detection by display of double peaks or bands, i.e. "peak doubling". Thus, atropisomerically enriched or purified forms of xanthene dyes are important as labels for methods based on separation and detection of analytes.

SUMMARY

The present invention is directed towards atropisomerically-enriched and substantially pure atropisomers of asymmetric xanthene compounds as novel compositions. The invention also includes methods for isolation, labelling, and detecting labelled compositions.

In a first aspect, the invention includes substantially pure atropisomer compounds having the structure II:

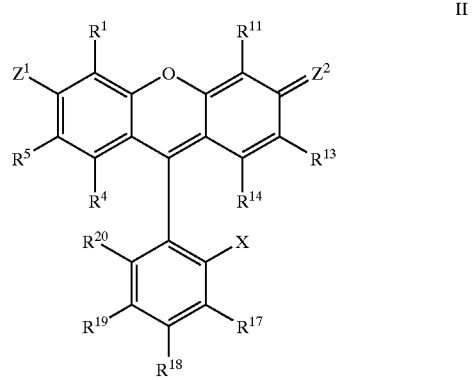

II wherein positions $R^1$, $R^4$, $R^5$, $R^{11}$, $R^{13}$, $R^{14}$, $R^{17}$, $R^{18}$, $R^{19}$, $R^{20}$, $Z^1$, or $Z^2$ may be substituted with substituents. At least one substituent may be a linking moiety. One or more rings may be fused to the ring structure II.

Another aspect of the invention includes energy-transfer dye compounds comprising a donor dye capable of absorbing light at a first wavelength and emitting excitation energy in response thereto; an acceptor dye capable of absorbing the excitation energy emitted by the donor dye and fluorescing at a second wavelength in response; and a linker for linking the donor dye and the acceptor dye; wherein at least one of the donor dye and acceptor dye is a substantially pure atropisomer of a xanthene compound.

Another aspect of the invention is labelled substrates, including nucleoside, nucleotides, polynucleotides, and polypeptides wherein the label is a substantially pure atropisomer of a xanthene compound or an energy-transfer dye comprising a substantially pure atropisomer of a xanthene compound.

Another aspect of the invention is labelling reagents, including phosphoramidite and active ester linking moieties of a substantially pure atropisomer of a xanthene compound, which form covalent attachments with substrates and methods of labelling substrates with the reagents.

Another aspect of the invention is methods for forming a labelled substrate comprising the step of reacting a substrate with the linking moiety of a substantially pure atropisomer of a xanthene compound or an energy-transfer dye comprising a substantially pure atropisomer of a xanthene compound.

Another aspect of the invention is methods for separating atropisomers of xanthene compounds by forming diastereomers with substantially enantiomerically pure compounds, and separating the diastereomers. The diastereomers may be converted to substantially pure atropisomers of xanthene compounds.

Another aspect of the invention is methods for separating a mixture of labelled substrates wherein the labels are comprised of a substantially pure atropisomer of a xanthene compound or an energy-transfer dye comprising a substantially pure atropisomer of a xanthene compound. The labelled substrates may be primer extension polynucleotide fragments. The labelled substrates may be separated by electrophoresis, chromatography, or other separation technique. The mixture of labelled polynucleotides may be formed from a labelled primer or a labelled terminator. The labelled substrates may be detected by fluorescence detection.

Another aspect of the invention is methods of generating a labelled primer extension product by extending a primer-target hybrid with an enzymatically-incorporatable nucleotide. The primer or the nucleotide may be labelled with a substantially pure atropisomer of a xanthene compound or an energy-transfer dye comprising a substantially pure atropisomer of a xanthene compound.

Another aspect of the invention is methods of polynucleotide sequencing by forming a mixture of four classes of polynucleotides where each class is labelled at the 3' terminal nucleotide with a substantially pure atropisomer of a xanthene compound or an energy-transfer dye comprising a substantially pure atropisomer of a xanthene compound, and the labels are spectrally resolvable. The polynucleotides are separated by size.

Another aspect of the invention is methods of oligonucleotide ligation by annealing two probes to a target sequence and forming a phosphodiester bond between the 5' terminus of one probe and the 3+ terminus of the other probe wherein one or both probes are labelled with a substantially pure atropisomer of a xanthene compound or an energy-transfer dye comprising a substantially pure atropisomer of a xanthene compound.

Another aspect of the invention is methods of amplification by annealing two or more primers to a target polynucleotide and extending the primers by a polymerase and a mixture of enzymatically-extendable nucleotides wherein at least one of the primers or one of the nucleotides is labelled with a substantially pure atropisomer of a xanthene compound or an energy-transfer dye comprising a substantially pure atropisomer of a xanthene compound.

Another aspect of the invention is kits of reagents including a substantially pure atropisomer of a xanthene compound or an energy-transfer dye comprising a substantially pure atropisomer of a xanthene compound.

DETAILED DESCRIPTION OF EXEMPLARY EMBODIMENTS

Figure 1A:
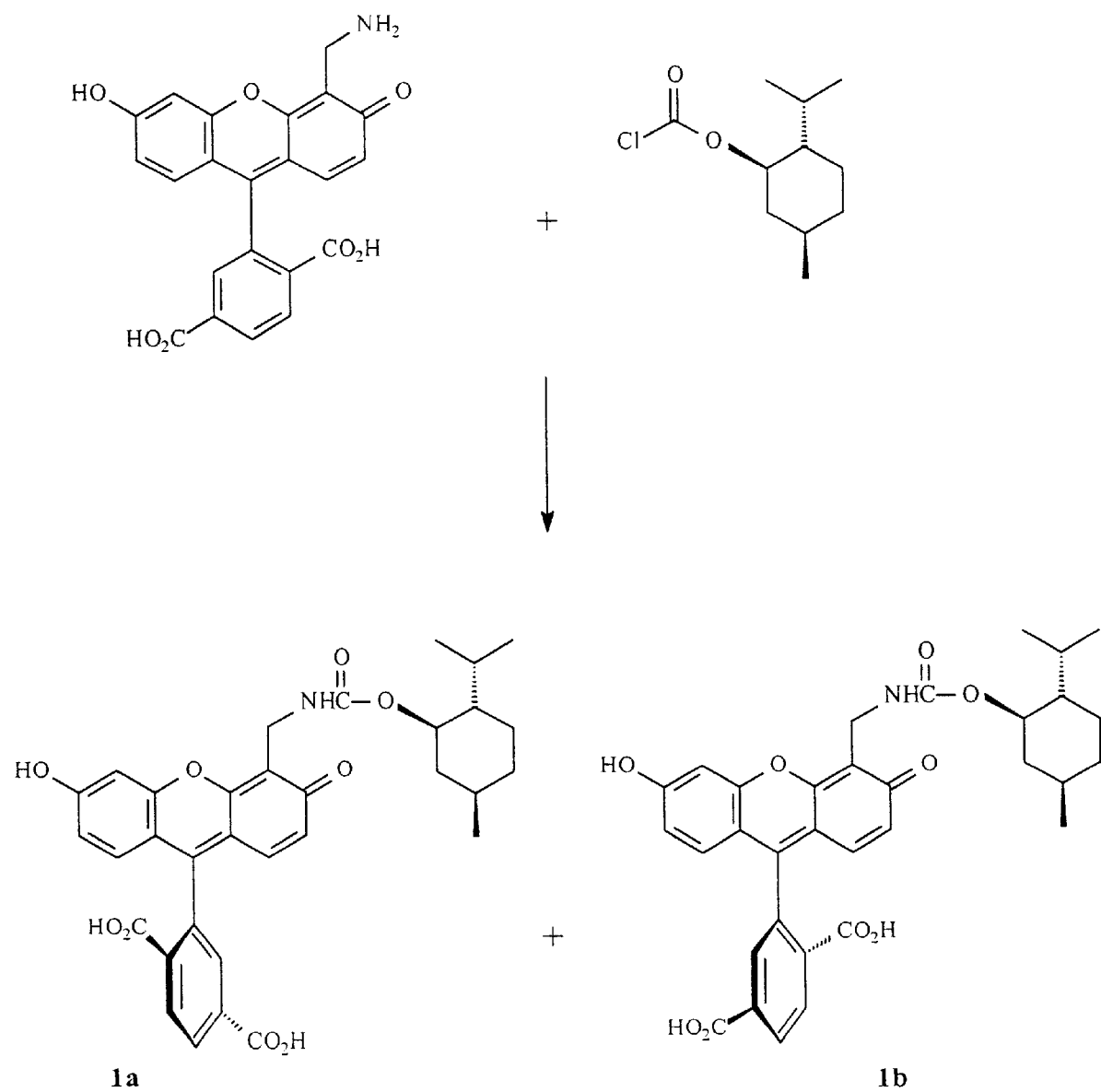
FIG. 1a shows the reaction of C-1 aminomethyl, C-19 carboxy fluorescein and (−) Menthyl chloroformate to give menthyl carbamate diastereomers 1a and 1b.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the scope of the claimed invention.

Definitions

Stereochemical definitions and conventions used herein generally follow *McGraw-Hill Dictionary of Chemical Terms* (1984) S. P. Parker, Ed., McGraw-Hill Book Company, New York and *Stereochemistry of Organic Compounds* (1994); and Eliel, E. and Wilen, S., John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate. The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "atropisomer" refers to a stereoisomer resulting from restricted rotation about single bonds where the rotation barrier is high enough to permit isolation of the isomeric species. Atropisomers are enantiomers without a single asymmetric atom. Atropisomers are conformational stereoisomers which occur when rotation about a single bond in the molecule is prevented, or greatly slowed, as a result of steric interactions with other parts of the molecule and the substituents at both ends of the single bond are unsymmetrical.

The terms "substantially pure atropisomer" and "substantially free of its stereoisomer" mean that the composition contains at least 90% by weight of one atropisomer, and 10% by weight or less of the stereoisomeric atropisomer.

The term "atropisomerically enriched" means that the composition is a greater proportion or percentage of one of the atropisomers of the xanthene compound, in relation to the other atropisomer.

"Nucleobase" means a nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine (Kutyavin, U.S. Pat. No. 5,912,340), inosine, nebularine, nitropyrrole, nitroindole, 2-aminopurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methyl-indole, and ethenoadenine (Fasman (1989) *Practical Handbook of Biochemistry and Molecular Biology*, pp. 385–394, CRC Press, Boca Raton, Fla.).

"Nucleoside" means a compound consisting of a nucleobase linked to the C-1' carbon of a ribose sugar. The ribose may be substituted or unsubstituted. Substituted ribose sugars include, but are not limited to, those riboses in which one or more of the carbon atoms, e.g., the 3'-carbon atom, is substituted with one or more of the same or different —R, —OR, —NRR or halogen groups, where each R is independently hydrogen, $C_1$–$C_6$ alkyl or $C_5$–$C_{14}$ aryl. Riboses include ribose, 2'-deoxyribose, 2',3'-dideoxyribose, 3'-haloribose, 3'-fluororibose, 3'-chlororibose, 3'-alkylribose, e.g. 2'-O-methyl, 4-α-anomeric nucleotides, 1'-α-anomeric nucleotides, and 2'-4'-linked and other "locked", bicyclic sugar modifications (Imanishi WO 98/22489; Imanishi WO 98/39352; Wengel WO 99/14226). When the nucleobase is purine, e.g. A or G, the ribose sugar is attached to the $N^9$-position of the nucleobase. When the nucleobase is pyrimidine, e.g. C, T or U, the pentose sugar is attached to the $N^1$-position of the nucleobase (Kornberg and Baker, (1992) *DNA Replication*, $2^{nd}$ Ed., Freeman, San Francisco, Calif.).

"Nucleotide" means a phosphate ester of a nucleoside, as a monomer unit or within a nucleic acid. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5' position. The triphosphate ester group may include sulfur substitutions for the various oxygens, e.g. α-thio-nucleotide 5'-triphosphates.

As used herein, the terms "oligonucleotide" and "polynucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of internucleotide, nucleobase and sugar analogs. Polynucleotides typically range in size from a few monomeric units, e.g. 5–40, when they are frequently referred to as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Attachment site" means a site on a label or a substrate, such as an oligonucleotide, which is covalently attached to a linker.

"Linker" means a chemical moiety comprising a covalent bond or a chain of atoms that covalently attaches a label to a polynucleotide, or one label to another.

"Linking moiety" means a chemically reactive group, substituent or moiety, e.g. a nucleophile or electrophile, capable of reacting with another molecule to form a covalent bond, or linkage.

"Alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1–12 saturated and/or unsaturated carbons, including, but not limited to, methyl, ethyl, propyl, butyl, and the like.

"Alkoxy" means —OR where R is ($C_1$–$C_6$) alkyl.

"Alkyldiyl" means a saturated or unsaturated, branched, straight chain or cyclic hydrocarbon radical of 1–20 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl, 1,3-propyldiyl, 1,4-butyldiyl, and the like.

"Aryl" means a monovalent aromatic hydrocarbon radical of 6–20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Aryldiyl" means an unsaturated cyclic or polycyclic hydrocarbon radical of 6–20 carbon atoms having a conjugated resonance electron system and at least two monovalent radical centers derived by the removal of two hydrogen atoms from two different carbon atoms of a parent aryl compound.

"Substituted alkyl", "substituted alkyldiyl", "substituted aryl" and "substituted aryldiyl" mean alkyl, alkyldiyl, aryl and aryldiyl respectively, in which one or more hydrogen atoms are each independently replaced with another substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —NCO, —NCS, —NO, —NO$_2$, =N$_2$, —N$_3$, NC(O)R, —C(O)R, —C(O)NRR —S(O)$_2$O$^-$, —S(O)$_2$OH, —S(O)$_2$R, —OS(O)$_2$OR, —S(O)$_2$NR, —S(O)R, —OP(O)O$_2$RR, —P(O)O$_2$RR —P(O)(O$^-$)$_2$, —P(O)(OH)$_2$, —C(O)R, —C(O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen and each R is independently —H, alkyl, aryl, heterocycle, or linking group.

"Internucleotide analog" means a phosphate ester analog of an oligonucleotide such as: (i) alkylphosphonate, e.g. $C_1$–$C_4$ alkylphosphonate, especially methylphosphonate; (ii) phosphoramidate; (iii) alkylphosphotriester, e.g. $C_1$–$C_4$ alkylphosphotriester; (iv) phosphorothioate; and (v) phosphorodithioate. Internucleotide analogs also include non-phosphate analogs wherein the sugar/phosphate subunit is replaced by an a non-phosphate containing backbone structure. One type of non-phosphate oligonucleotide analogs has an amide linkage, such as a 2-aminoethylglycine unit, commonly referred to as PNA (Nielsen (1991) "Sequence-selective recognition of DNA by strand displacement with a thymidine-substituted polyamide", Science 254:1497–1500).

The terms "target sequence" and "target polynucleotide" mean a polynucleotide sequence that is the subject of hybridization with a complementary polynucleotide, e.g., a primer or probe. The sequence can be composed of DNA, RNA, an analog thereof, including combinations thereof.

The term "label", as used herein, means any moiety which can be attached to a substrate, e.g., an oligonucleotide, nucleotide or nucleotide 5'-triphosphate, and that functions to: (i) provide a detectable signal; (ii) interact with a second label to modify the detectable signal provided by the first or second label, e.g. FRET; (iii) stabilize hybridization, i.e. duplex formation; (iv) affect mobility, e.g. electrophoretic mobility or cell-permeability, by charge, hydrophobicity, shape, or other physical parameters, or (v) provide a capture moiety, e.g., affinity, antibody/antigen, or ionic complexation.

"Heterocycle" means a molecule with a ring system in which one or more ring atoms have been replaced with a heteroatom, e.g. nitrogen, oxygen, and sulfur.

"Electron-deficient nitrogen heterocycle" is a monovalent electron-deficient nitrogen heterocycle derived by the removal of one hydrogen atom from a single atom of the ring system to join the heterocycle as a substituent to the fluorescein dyes of the invention (Joule, *Heterocyclic Chemistry*, 3rd Ed., Stanley Thornes Publisher, Ltd., Cheltenham, U.K. (1998); Acheson, R., *An Introduction to the Chemistry of Heterocyclic Compounds*, 2nd Ed. Interscience Publishers, division of John Wiley & Sons, New York (1967)).

"Substrate" is an entity to which dye compounds of the present invention are attached. Substrates include, but are not limited to a (i) polynucleotide, (ii) nucleoside and nucleotide, (iii) polypeptide, (iv) carbohydrate, (v) ligand, and (vi) any analog of the preceding (i) to (v). "Enzymatically incorporatable" is a property of a nucleotide in which it is capable of being enzymatically incorporated onto the terminus, e.g. 3', of a nascent polynucleotide chain through the action of a polymerase enzyme.

"Terminator" means an enzymatically incorporatable nucleotide which prevents subsequent incorporations of nucleotides to the resulting polynucleotide chain and thereby halt polymerase extension. Typical terminators lack a 3'-hydroxyl substituent and include 2',3'-dideoxyribose, 2',3'-didehydroribose, and 2',3'-dideoxy, 3'-haloribose, e.g. 3'-fluoro. Alternatively, a ribofuranose analog could be used, such as arabinose. Exemplary nucleotide terminators include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (Chidgeavadze (1984) Nucleic Acids Res., 12: 1671–1686; and Chidgeavadze (1985) FEB. Lett., 183: 275–278). Nucleotide terminators also include reversible nucleotide terminators (Metzker (1994) Nucleic Acids Res., 22(20): 4259).

"Enzymatically extendable" is a property of a nucleotide in which it is enzymatically incorporatable at the terminus of a polynucleotide and the resulting extended polynucleotide can undergo subsequent incorporations of nucleotides or nucleotide analogs.

Atropisomer Compounds

The compositions of the invention are asymmetric xanthene compounds that exist in stable atropisomeric forms. Aryl substituents can restrict rotation around the biannular bond between C-10 and C-15 (noted by an arrow) in the following structure I:

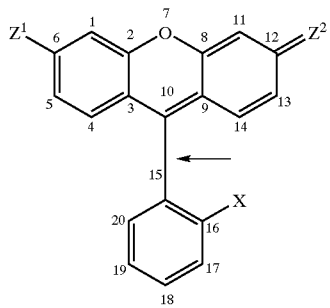

Asymmetric compounds of the invention include xanthene dyes characterized by the general structure II:

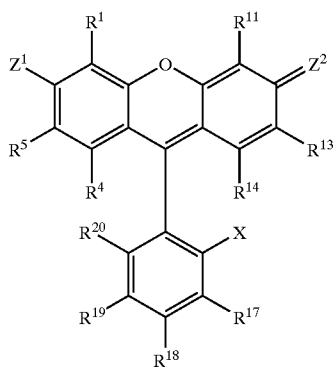

and include asymmetric fluorescent dye classes such as fluorescein ($Z^1$, $Z^2$=O), rhodol ($Z^1$=O, $Z^2$=NR$_2$), and rhodamine ($Z^1$, $Z^2$=NR$_2$). Where $Z^1$ or $Z^2$ is NR$_2$, R may independently be hydrogen, $C_1$–$C_{12}$ alkyl, phenyl, benzyl, aryl, heterocycle, or a linking moiety.

Substituents $R^1$, $R^4$, $R^5$, $R^{11}$, $R^{13}$, $R^{14}$, $R^{17}$, $R^{18}$, $R^{19}$, and $R^{20}$ may be independently fluorine, chlorine, $C_1$–$C_8$ alkyl, carboxylate, sulfate, sulfonate (—SO$_3^-$), alkylsulfonate (—R—SO$_3^-$), aminomethyl (—CH$_2$NH$_2$), aminoalkyl, 4-dialkylaminopyridinium, hydroxymethyl (—CH$_2$OH), methoxy (—OCH$_3$), hydroxyalkyl (—ROH), thiomethyl (—CH$_2$SH), thioalkyl (—RSH), alkylsulfone (—SO$_2$R), arylthio (—SAr), arylsulfone (—SO$_2$Ar), sulfonamide (—SO$_2$NR$_2$), alkylsulfoxide (—SOR), arylsulfoxide (—SOAr), amino (—NH$_2$), ammonium (—NH$_3^+$), amido (—CONR$_2$), nitrile (—CN), $C_1$–$C_8$ alkoxy (—OR), phenoxy, phenolic, tolyl, phenyl, aryl, benzyl, heterocycle, phosphonate, phosphate, quaternary amine, sulfate, polyethyleneoxy, and linking moiety.

The compounds of the invention include fused benzo rings where $R^{13}$ and $R^{14}$, or $R^4$ and $R^5$, taken together form benzo, and where the fused benzo groups are substituted with substituents.

Substituents $R^1$, $R^4$, $R^5$, $R^{11}$, $R^{13}$, $R^{14}$, $R^{17}$, $R^{18}$, $R^{19}$, and $R^{20}$ may also be independently an electron-deficient heterocycle, including 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, pthalazine, quinazoline, quinoxaline, 3-(1,2,4-N)-triazolyl, 5-(1,2,4-N)-triazolyl, 5-tetrazolyl, 4-(1-O, 3-N)-oxazole, 5-(1-O, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, or benzimidazole.

Examples of asymmetric fluorescein dyes include the structures:

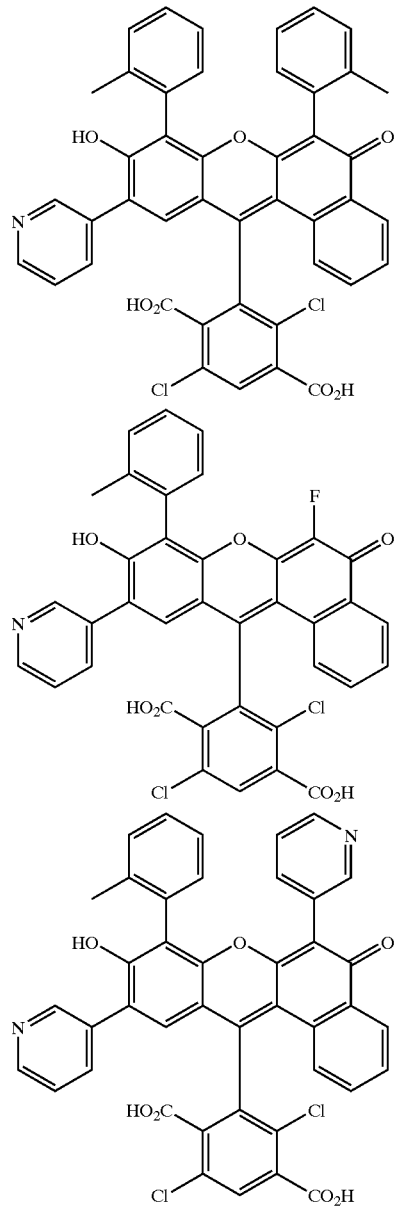

The compounds of the invention include atropisomeric, asymmetric rhodamines with ring structures formed by the $Z^1$ nitrogen, the $Z^1$-bonded carbon, and the $R^1$-bonded carbon, to make a first ring structure having from 4 to 7 members. Optionally, the compounds may have a second ring structure formed by the $Z^2$ nitrogen, the $Z^2$-bonded carbon, and the $R^{11}$-bonded carbon, also having from 4 to 7 members. An example includes the structure IIa:

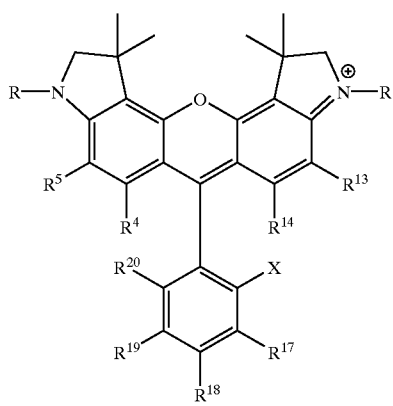

IIa

Asymmetry results where either: (1) $R^1 \neq R^{11}$, $R^4 \neq R^{14}$, $R^5 \neq R^{13}$, or $Z^1 \neq Z^2$, and (2) $R^{17} \neq R^{19}$, or $R^{20} \neq X$. In other words, both aryl substituents on the biannular sp2-sp2 bond are asymmetric and the compound lacks a $C_2$ axis of symmetry along the biannular bond axis. $C_2$ symmetry is defined by taking the biannular bond in I or II as the axis such that rotation of 180° around the axis, gives the same molecule. An example of a symmetric xanthene compound with $C_2$ symmetry is fluorescein ($R^1$, $R^4$, $R^5$, $R^{11}$, $R^{13}$, $R^{14}$, $R^{17}$, $R^{18}$, $R^{19}$, $R^{20}$=H; X=CO$_2$H). An example of an asymmetric xanthene compound without $C_2$ symmetry is C-11 aminomethyl, C-19 carboxyfluorescein ($R^1$, $R^4$, $R^5$, $R^{13}$, $R^{14}$, $R^{17}$, $R^{18}$, $R^{20}$=H; $R^{11}$=CH$_2$NH$_2$; $R^{19}$, X=CO$_2$H). This compound is atropisomeric because the substituents adjacent to the C-10 to C-15 biannular bond are sufficiently bulky that rotation is hindered. The energy barrier to rotation is sufficiently high that stable, non-superimposable, mirror image atropisomeric forms 2a and 2b result, as shown:

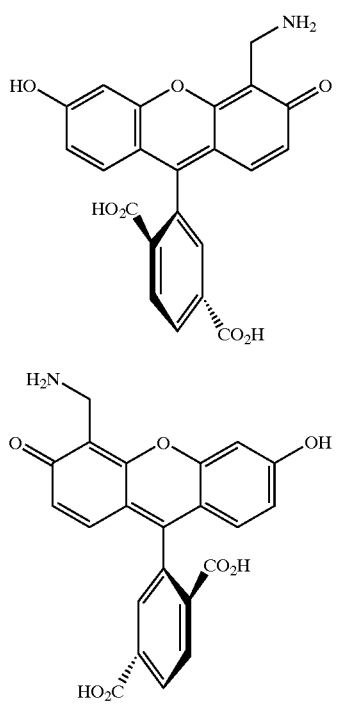

2a

2b

Rotation around the biannular bond results in racemization and loss of atropisomerism. Typically, racemization of the asymmetric xanthene compounds occurs upon heating.

The compounds of the present invention can be prepared by any suitable method available in the art. Exemplary methods for preparing a variety of different asymmetric xanthene compounds can be found in the Example section below, and as discussed in greater detail below.

As a specific example, reference is made throughout the specification to $Z^1$ and $Z^2$ substituents. As this nomenclature corresponds to the illustrated structural formulae, which represent only one of several possible tautomeric forms (or resonance structures) of the compounds, it will be understood that these references are for convenience only, and that any such references are not intended to limit the scope of the compounds described herein.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The compounds of the invention may bear multiple positive or negative charges. The net charge of the dyes of the invention may be either positive or negative. The counter ions associated with the dyes are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the dyes in association with any type of counter ion. Moreover, as the compounds can exists in a variety of different forms, the invention is intended to encompass not only forms of the dyes that are in association with counter ions (e.g., dry salts), but also forms that are not in association with counter ions (e.g., aqueous or organic solutions).

Asymmetric xanthene compounds can be conveniently synthesized from precursors (U.S. Pat. Nos. 5,188,934; 5,654,442; 5,885,778; 6,096,723; 6,020,481; 5,863,727; 5,800,996; 5,945,526; 5,847,162; 6,025,505; 6,008,379; 5,936,087; 6,015,719). An exemplary synthetic route starts by aminomethylation of C-19 carboxyfluorescein (Shipchandler (1987) Anal. Biochem. 162:89–101; U.S. Pat. No. 4,510,251; EP 232736; EP 110186) to give C-1 (C-11) aminomethyl, C-19 carboxyfluorescein.

An atropisomer substantially free of its stereoisomer may be obtained by resolution of the mixture of stereoisomers of a xanthene compound using a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283–302). Atropisomers of xanthene dyes can be separated and isolated, prior to, or after, derivatization to give reactive labelling reagents. Separation of the atropisomer xanthene compounds of the invention from the racemic mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure atropisomers, and (3) separation of the atropisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric xanthene compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds,* John Wiley & Sons, Inc., p. 322). Diastereomeric compounds can be formed by reacting asymmetric xanthene compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, α-methoxy-α-(trifluoromethyl)phenyl acetate (Jacob III. (1982) J. Org. Chem. 47:4165), of the racemic mixture, and analyzing the NMR spectrum for the presence of the two atropisomeric diastereomers. For example, C-1 aminomethyl, C-19 carboxy fluorescein, an asymmetric xanthene compound useful for attaching to nucleotides, polynucleotides, and other fluorescent dyes was reacted with (−) menthyl chloroformate in the presence of base to form the diastereomeric mixture of menthyl carbamates 1a and 1b (Example 1, FIG. 1*a*). Stable diastereomers of atropisomeric xanthene compounds can be separated and isolated by normal- and reverse-phase chromatography following methods for separation of atropisomeric naphthyl-isoquinolines (Hoye, T., WO 96/15111). Diastereomers 1a and 1b were separated by preparative reverse-phase HPLC (Example 2, FIG. 1*b*).

Figure 2A:
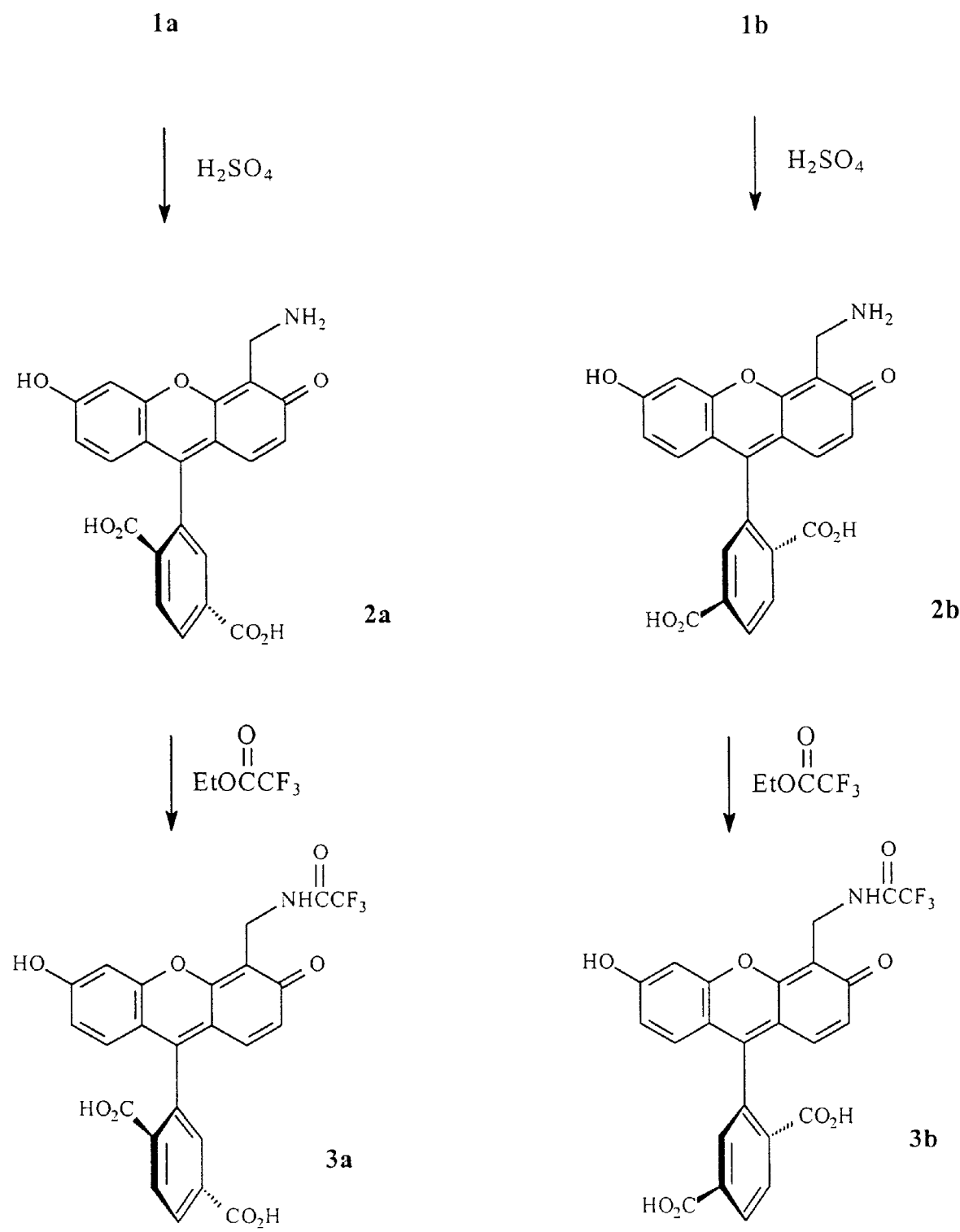
FIG. 2a shows the reactions of: (i) menthyl carbamate diastereomer 1a with sulfuric acid to hydrolyze the menthyl carbamate group to give atropisomer amine 2a, (ii) amidation of 2a with ethyl trifluoroacetate to give atropisomer trifluoroacetamide 3a, (iii) menthyl carbamate diastereomer 1b with sulfuric acid to hydrolyze the menthyl carbamate group to give atropisomer amine 2b, and (iv) amidation of 2b with ethyl trifluoroacetate to give atropisomer trifluoroacetamide 3b.
Figure 2B:
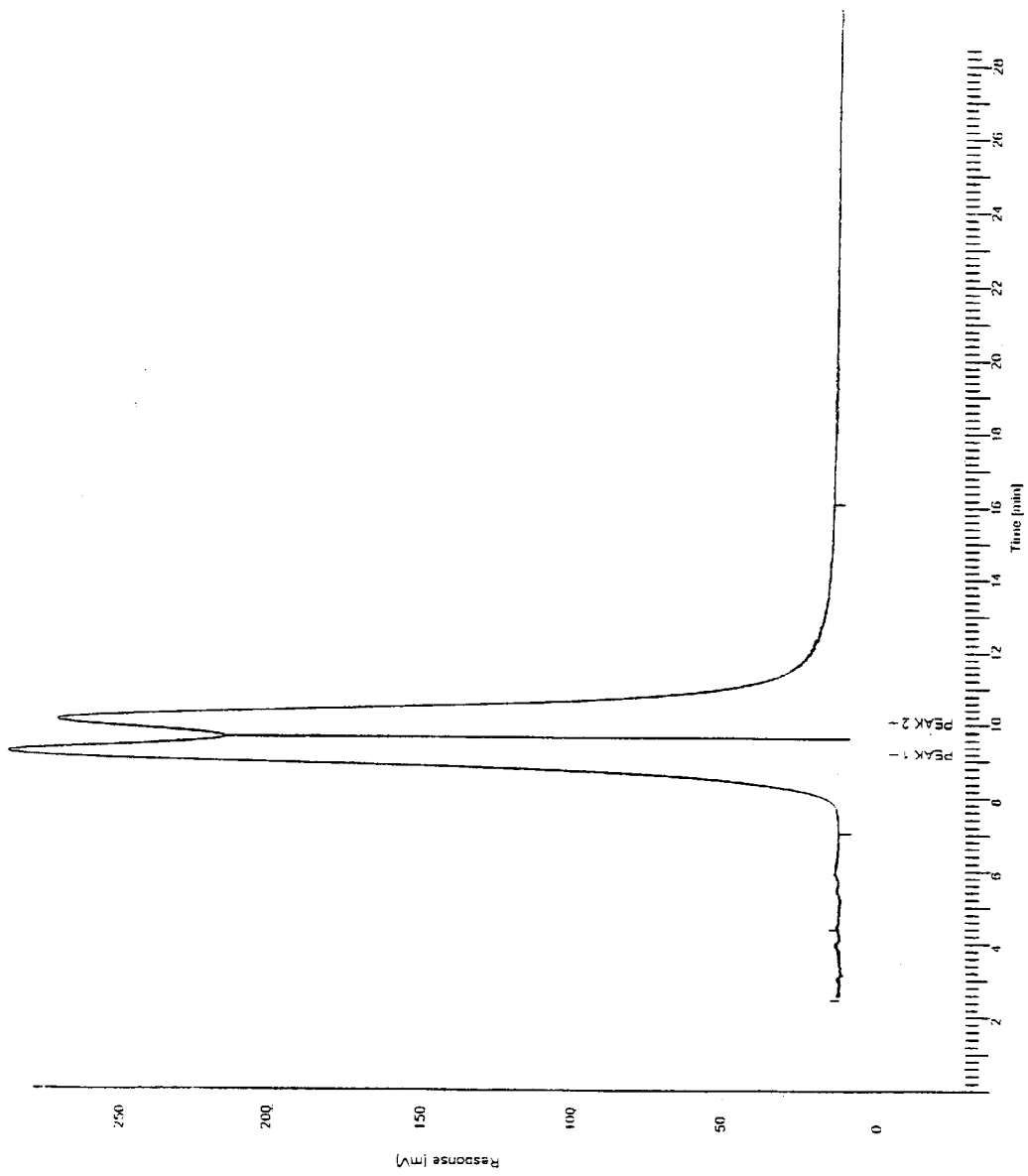
FIG. 2b shows an HPLC chromatogram of the racemic mixture of atropisomers 2a and 2b under chiral HPLC conditions.
Figure 2C:
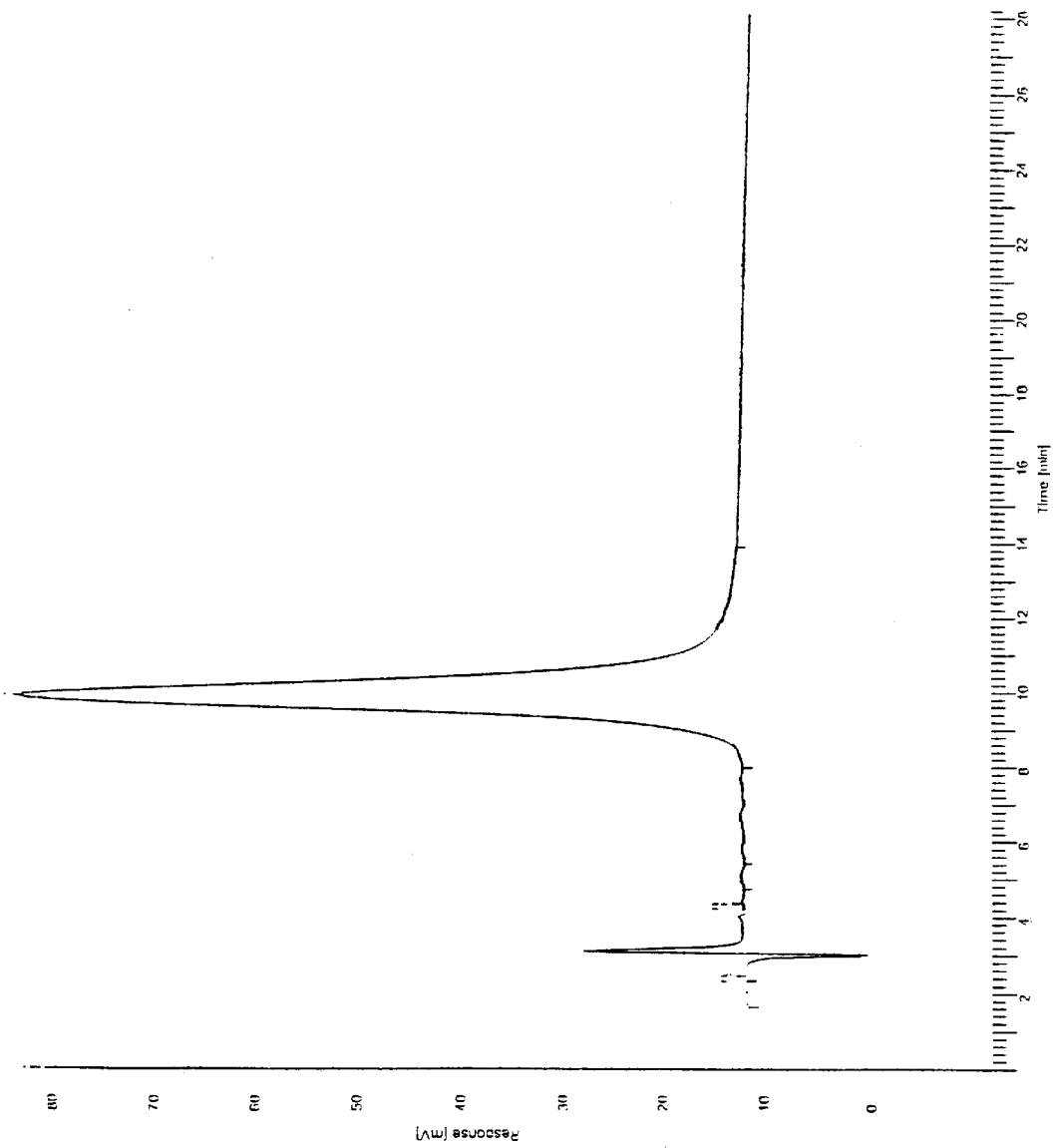
FIG. 2c shows an HPLC chromatogram of the purified atropisomer 2a under chiral HPLC conditions.

By method (3), a racemic mixture of two asymmetric enantiomers can be separated by chromatography using a chiral stationary phase ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375–378). Enantiomeric atropisomers of xanthene compounds can be separated and isolated by chromatography on chiral stationary phase. A sample of racemic, C-1 aminomethyl, C-19 carboxy fluorescein gave two peaks, resolving the atropisomeric stereoisomers, by HPLC analysis on a chiral adsorbent column (FIG. 2*b*). When the atropisomers are separated, for example, by the chiral derivatization method (Example 1), preparative HPLC separation (Example 2) and hydrolysis of the chiral menthyl auxiliaries (Example 3, FIG. 2*a*), the separated atropisomer 2a showed a single peak when analyzed by HPLC on the chiral adsorbent column (FIG. 2*c*).

Atropisomers can be distinguished by methods used to distinguish other chiral molecules with asymmetric carbon atoms, such as optical rotation and circular dichroism.

Energy-Transfer Dyes

In another aspect, the present invention comprises energy-transfer dye compounds containing atropisomeric xanthene compounds such as those defined by structure II. Generally, the energy-transfer dyes of the present invention include a donor dye which absorbs light at a first wavelength and emits excitation energy in response, an acceptor dye which is capable of absorbing the excitation energy emitted by the donor dye and fluorescing at a second wavelength in response. The donor dye may be attached to the acceptor dye through a linker, the linker being effective to facilitate efficient energy transfer between the donor and acceptor dyes (Lee, "Energy-transfer dyes with enhanced fluorescence", U.S. Pat. No. 5,800,996; Lee "Energy-transfer dyes with enhanced fluorescence", U.S. Pat. No. 5,945,526; Mathies, "Fluorescent labels and their use in separations", U.S. Pat. No. 5,654,419; Lee (1997) Nucleic Acids Res. 25:2816–22). Alternatively, the donor dye and the acceptor dye may be labelled at different attachment sites on the substrate. For example, an oligonucleotide may be labelled with a donor dye at the 5' terminus and an acceptor dye at the 3' terminus. A polypeptide may be labelled with a donor dye at the carboxyl terminus and an acceptor dye at an internal cysteine or lysine sidechain (Komoriya, "Compositions for the detection of proteases in biological samples and methods of use thereof", U.S. Pat. No. 5,605,809). In the energy-transfer dye of the invention, at least one of the donor or acceptor dyes which label a substrate is an atropisomeric xanthene compounds. Other dyes comprising the energy-transfer dye may be any fluorescent moiety which undergoes the energy transfer process with an atropisomeric xanthene compound, including a fluorescein, rhodol, and a rhodamine. Other dyes include classes of fluorescent dyes such as cyanine, phthalocyanine, squaraine, bodipy, benzophenoxazine, fluorescein, dibenzorhodamine, or rhodamine.

Energy-transfer dyes have advantages for use in the simultaneous detection of multiple labelled substrates in a mixture, such as DNA sequencing. A single donor dye can be used in a set of energy-transfer dyes so that each dye has strong absorption at a common wavelength. By then varying the acceptor dye in the energy-transfer set, the acceptor dyes can be spectrally resolved by their respective emission maxima. Energy-transfer dyes also provide a larger effective Stokes shift than non-energy-transfer dyes. The Stokes shift is the difference between the excitation maximum, the wavelength at which the donor dye maximally absorbs light, and the emission maximum, the wavelength at which the acceptor maximally emits light.

Generally the linker between the donor dye and acceptor dye has the structures:

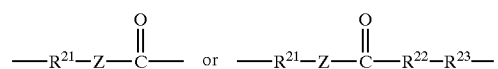

wherein Z is selected from the group consisting of NH, S and O; $R^{21}$ is a $C_1$–$C_{12}$ alkyl attached to the donor dye; $R^{22}$ is a substituent selected from the group consisting of a $C_1$–$C_{12}$ alkyldiyl, a five and six membered ring having at least one unsaturated bond and a fused ring structure which is attached to the carbonyl carbon; and $R^{23}$ includes a functional group which attaches the linker to the acceptor dye. $R^{22}$ may be a five or six membered ring such as cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene. Specifically, the linker may have the structure:

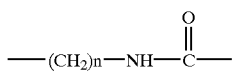

where n ranges from 2 to 10.

Generally also, $R^{23}$ may have the structure:

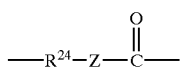

wherein $R^{24}$ is a $C_1$–$C_{12}$ alkyl and

In one embodiment, the linker between the donor dye and acceptor dye includes a functional group which gives the linker some degree of structural rigidity, such as an alkene, diene, an alkyne, a five and six membered ring having at least one unsaturated bond or a fused ring structure. The donor dye and the acceptor dye of the energy-transfer dye may be attached by linkers which have the exemplary structures:

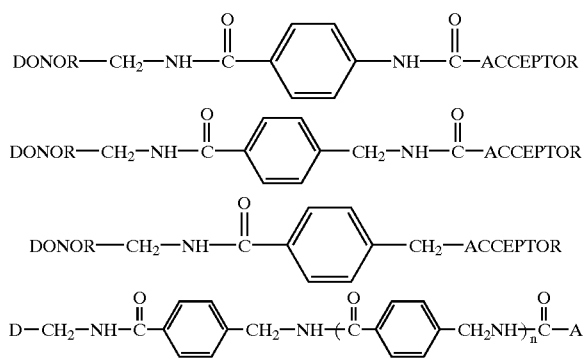

wherein D is a donor dye, A is an acceptor dye and n is 1 or 2. The phenyl rings may be substituted with groups such as sulfonate, phosphonate, and other charged groups.

The attachment sites of the linker between the donor dye and acceptor dye of an energy-transfer dye may be at any position where one or both of the donor dye and acceptor dye is a compound of the present invention. Exemplary attachment sites include $R^1$, $R^{11}$, $R^{18}$, $R^{19}$, $Z^1$ and $Z^2$. Examples of linkers and attachment sites are shown in terminator nucleotides 25, 26, 33, and 34 where the linkers attach at $R^1$ or $R^{11}$ of the donor fluorescein dye and at $R^{18}$ or $R^{19}$ of the acceptor rhodamine dye. An alternative embodiment is where the donor dye and the acceptor dye are attached by a linker through the $R^{18}$ or $R^{19}$ sites, and either the donor dye or the acceptor dye is attached to a substrate through the $R^1$, $R^{11}$, $Z^1$ or $Z^2$ site. Another alternative embodiment is where the donor dye and the acceptor dye are attached by a linker through the $R^1$, $R^{11}$, $Z^1$ or $Z^2$ sites, and either the donor dye or the acceptor dye is attached to a substrate through the $R^{18}$ or $R^{19}$ site.

The energy-transfer dye compound is covalently attached to a substrate through a linker. The linker may be a bond, $C_1$–$C_{12}$ alkyldiyl or $C_6$–$C_{20}$ aryldiyl. The linker may bear functional groups including amide, carbamate, urea, thiourea, phosphate, phosphonate, sulfonate, phosphorothioate, and the like. Preferred linkers include 1,2-ethyldiyl and 1,6-hexyldiyl. The attachment sites of the linker between the energy-transfer dye and the substrate may be at any position on the energy-transfer dye, where one or both of the donor dye and acceptor dye is a dye of the present invention. Where the substrate is a nucleoside or nucleotide, a preferred attachment site on the substrate is on the nucleobase. If the nucleobase is a purine, the linker may be attached at the 8-position. If the nucleobase is a 7-deazapurine, the linker may be attached at the 7-position or 8-position. If the nucleobase is a pyrimidine, the linker may be attached at the 5-position. As examples, in terminator nucleotide examples 25 and 26, the energy-transfer dye is attached to the nucleobase at $R^{19}$. Where the substrate is an oligonucleotide, preferred attachment sites include the 3' and 5' terminii. Other oligonucleotide attachment sites include the internucleotide phosphate, or phosphate-analog linkage, or at a position on the sugar, e.g. 2' or 4'. Where the substrate is a polypeptide (peptide or protein), preferred attachment sites include the amino and carboxyl termini, and lysine residue amino substituents.

Methods of Labelling

The present invention comprises labelling reagents wherein atropisomeric xanthene compounds are in reactive form to react with substrates. In another aspect, the present invention comprises substrates labelled, i.e. conjugated, with the compounds of the invention, formula I. Substrates can be virtually any molecule or substance to which the dyes of the invention can be conjugated, including by way of example and not limitation, a polynucleotide, a nucleotide, a nucleoside, a polypeptide, a carbohydrate, a ligand, a substantially enantiomerically pure compound, a particle, a surface, a lipid, a solid support, organic and inorganic polymers, and combinations and assemblages thereof, such as chromosomes, nuclei, living cells (e.g., bacteria or other microorganisms, mammalian cells, tissues, etc.), and the like. A particle may include a nanoparticle, a microsphere, a bead, or a liposome. A surface may be glass or other non-porous planar material. The compounds of the invention are conjugated with the substrate via an optional linker by a variety of means, including hydrophobic attraction, ionic attraction, and covalent attachment.

Labelling typically results from mixing an appropriate reactive atropisomeric xanthene and a substrate to be conjugated in a suitable solvent, using methods well-known in the art (Hermanson, *Bioconjugate Techniques,* (1996) Academic Press, San Diego, Calif. pp. 40–55, 643–71), followed by separation of the labelled substrate, conjugate, from any unconjugated starting materials or unwanted by-products. The conjugate can be stored dry or in solution for later use.

A racemic mixture of atropisomeric xanthenes may be separated to isolate substantially pure atropisomers at any intermediate stage in the synthesis of the labelling reagents, according to the aforementioned separation and isolation methods (1), (2), and (3).

The atropisomeric xanthene may include a linking moiety at one of the substituent positions or covalent attachment of the dye to another molecule. A linking moiety is typically an electrophilic functional group, capable of forming a covalent bond by reacting with nucleophilic functionality on a substrate. Nucleophilic functionality may include, for example, alcohols, alkoxides, amines, hydroxylamines, and thiols. Alternatively, a linking moiety may include nucleophilic functionality that reacts with an electrophilic group on a substrate. Examples of linking moieties include azido, monosubstituted primary amine, disubstituted secondary amine, thiol, hydroxyl, halide, epoxide, N-hydroxysuccinimidyl ester, carboxyl, isothiocyanate, sulfonyl chloride, sulfonate ester, silyl halide, chlorotriazinyl, succinimidyl ester, pentafluorophenyl ester, maleimide, haloacetyl, epoxide, alkylhalide, allyl halide, aldehyde, ketone, acylazide, anhydride, iodoacetamide and an activated ester.

Figure 4:
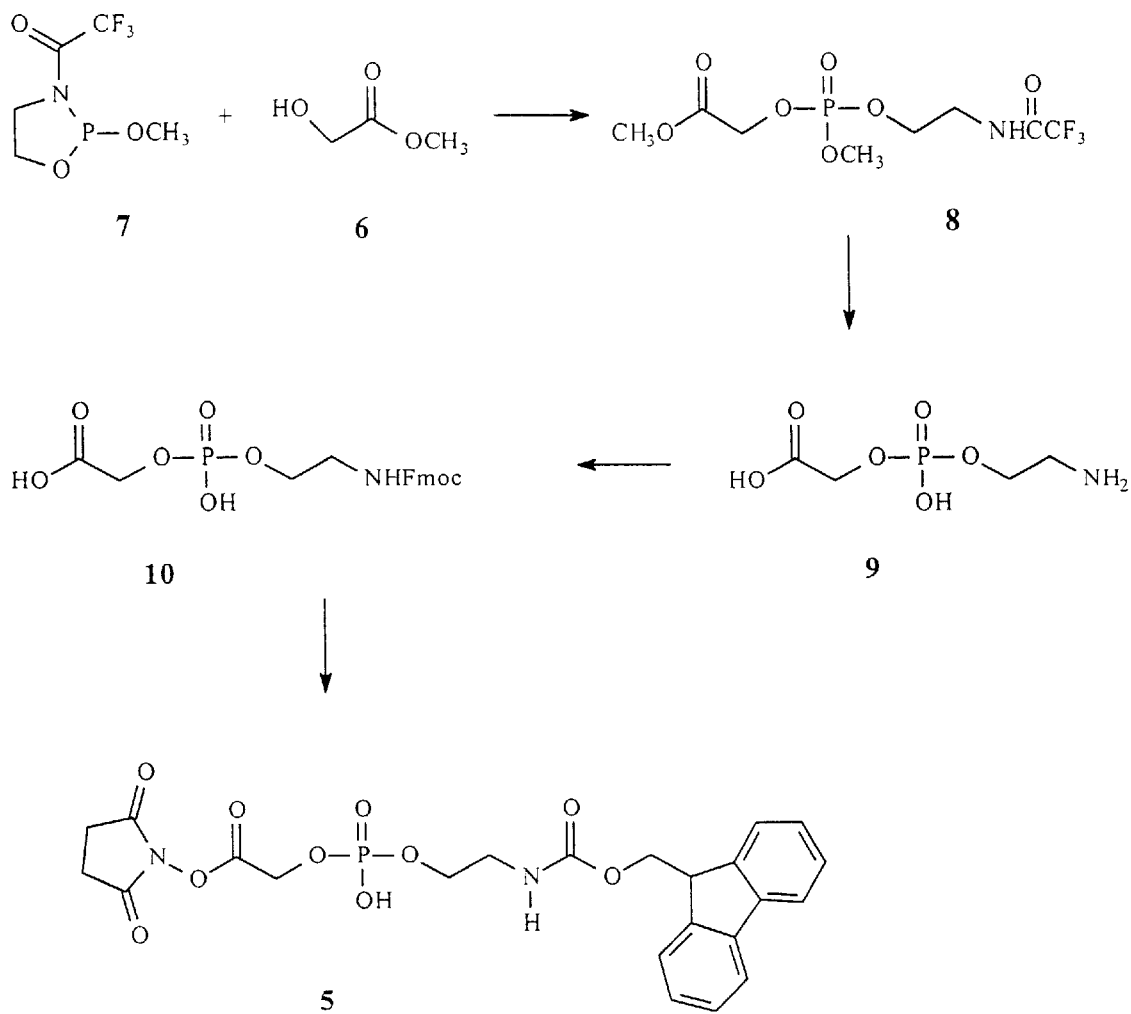
FIG. 4 shows the synthesis of 2-[(2-Fmoc-aminoethoxy)(hydroxyphosphoryl)oxy]acetic acid NHS 5.
Figure 5:
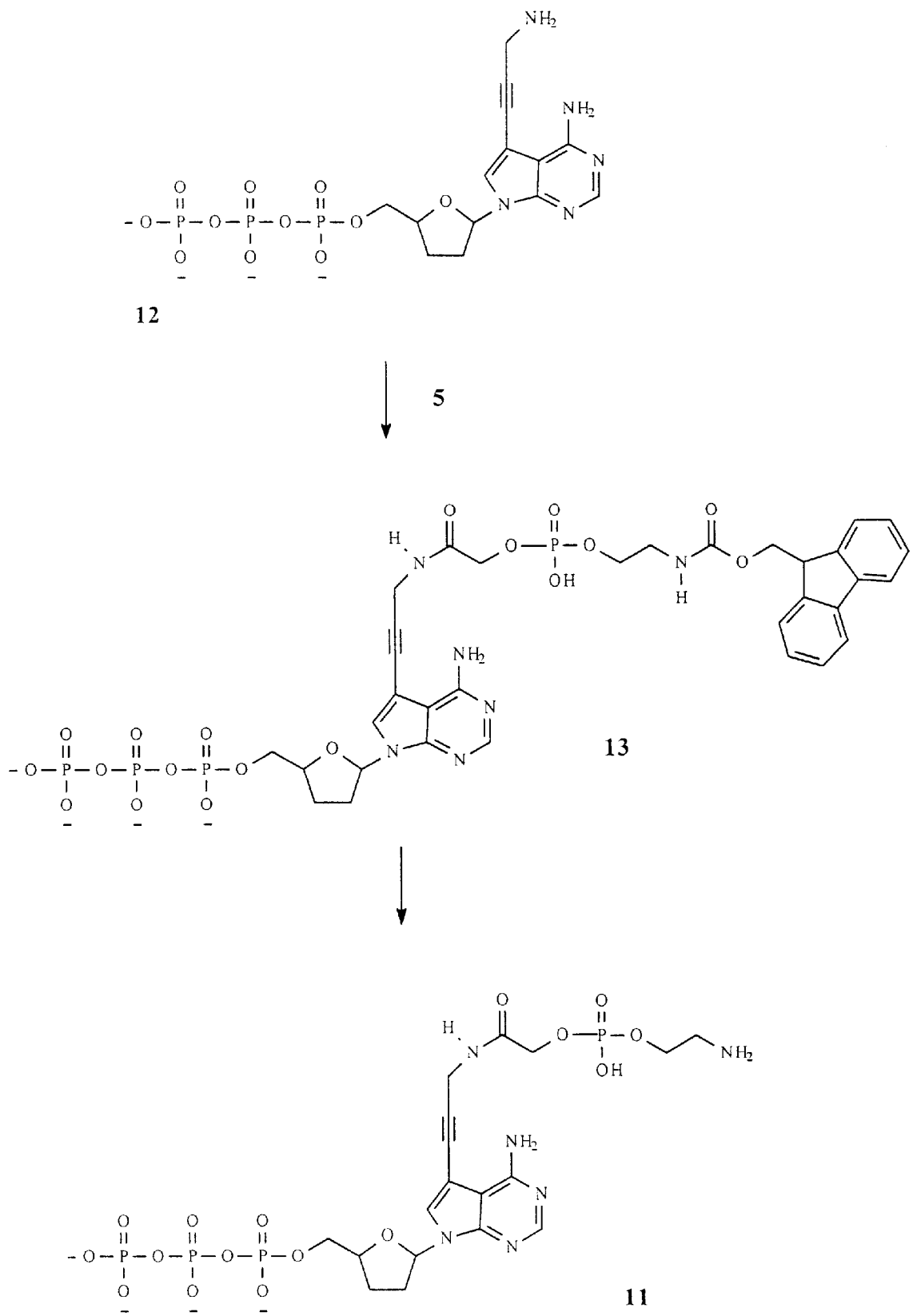
FIG. 5 shows the synthesis of propargylphosphorylamino-ddATP 11.

One linking moiety is N-hydroxysuccinimidyl ester (NHS) of a carboxyl group substituent of the atropisomeric xanthene compound (FIGS. 3, 6, 10, 11). The NHS ester form of the compound is a labelling reagent. The NHS ester of the dye may be preformed, isolated, purified, and/or characterized, or it may be formed in situ and reacted with a nucleophilic group of a substrate, such as an oligonucleotide, a nucleotide, a polypeptide, or the like (Brinkley, M. (1992) Bioconjugate Chem. 3:2–13). Typically, the carboxyl form of the dye is activated by reacting with some combination of: (1) a carbodiimide reagent, e.g. dicyclohexylcarbodiimide, diisopropylcarbodiimide, or a uronium reagent, e.g. TSTU (O-(N-Succinimidyl)-N,N,N',N'-tetramethyluronium tetrafluoroborate, HBTU (O-benzotriazol-1-yl)-N,N,N',N'-tetramethyluronium hexafluorophosphate), HATU (O-(7-azabenzotriazol-1-yl)-N,N,N',N'-tetramethyluronium hexafluorophosphate); (2) an activator, such as 1-hydroxybenzotriazole (HOBt); and (3) N-hydroxysuccinimide to give the NHS ester of the dye. A representative example of an NHS ester are structures 4a and 4b (FIG. 3), 8 (FIG. 4), and 13 (FIG. 5).

Figure 3:
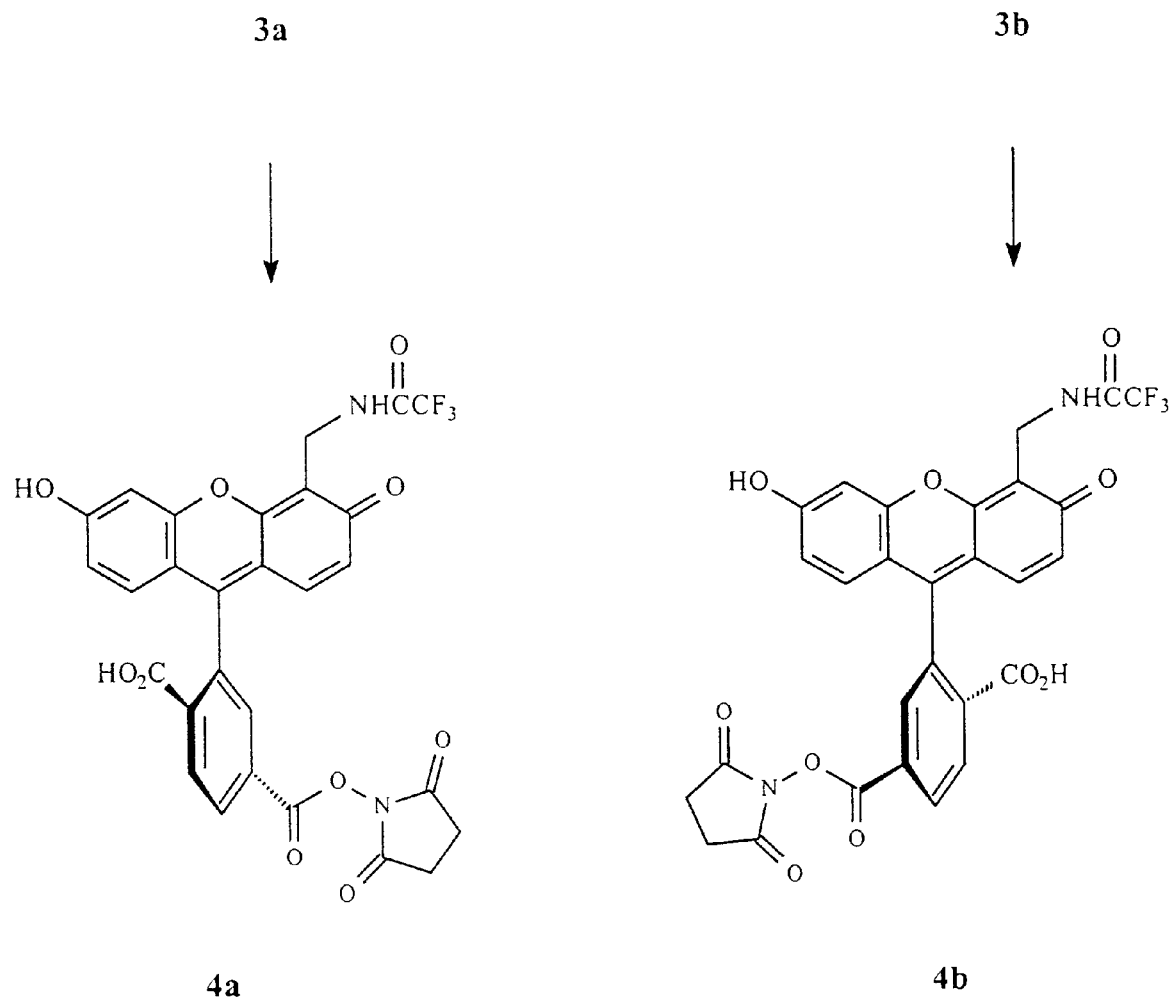
FIG. 3 shows the reactions of: (i) atropisomer trifluoroacetamide 3a with N-hydroxysuccinimide and DAE carbodiimide HCl salt to give atropisomeric NHS ester 4a, and (ii) atropisomer trifluoroacetamide 3b with N-hydroxysuccinimide and DAE carbodiimide HCl salt to give atropisomeric NHS ester 4b.

Functional groups on an atropisomeric xanthene compound may be protected prior to derivatization and reaction at other functional groups on the compound. For example, the amino group of atropisomers 2a and 2b were trifluoroacetylated to give 3a and 3b, separately (FIG. 2a, Examples 5 and 6). The carboxyl groups of were then converted to the active ester, NHS with N-hydroxysuccinimide and a carbodiimide reagent, e.g. DAE to give 4a and 4b, separately (FIG. 3, Examples 7 and 8).

In some cases, the atropisomeric xanthene compound and the substrate may be coupled by in situ activation of the compound and reaction with the substrate to form the atropisomeric xanthene-substrate conjugate in one step. Other activating and coupling reagents include TBTU (2-(1H-benzotriazo-1-yl)-1-1,3,3-tetramethyluronium hexafluorophosphate), TFFH (N,N',N",N'"-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Another preferred reactive linking group is a phosphoramidite form of asymmetric xanthene compounds. Phosphoramidite dye reagents are particularly useful for the automated synthesis of oligonucleotides labelled with the dyes of the invention. Most conveniently, phosphoramidite dye reagents may be coupled to oligonucleotides bound to a solid support during the normal course of solid-phase synthesis. Oligonucleotides are commonly synthesized on solid supports by the phosphoramidite method (Caruthers, M. and Beaucage, S. "Phosphoramidite compounds and processes", U.S. Pat. No. 4,415,732; Caruthers, M. and Matteucci, M. "Process for preparing polynucleotides", U.S. Pat. No. 4,458,066; Beaucage, S. and Iyer, R. (1992) "Advances in the synthesis of oligonucleotides by the phosphoramidite approach", Tetrahedron 48:2223–2311).

Phosphoramidite atropisomeric xanthene reagents can be nucleosidic or non-nucleosidic. Non-nucleosidic forms of the phosphoramidite reagents have the general formula III:

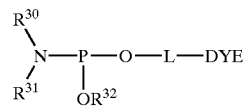

where DYE is a protected or unprotected form of atropisomer xanthene II, including energy-transfer dye; L is a linker; $R^{30}$ and $R^{31}$ taken separately are $C_1$–$C_{12}$ alkyl, $C_4$–$C_{10}$ aryl, and cycloalkyl containing up to 10 carbon atoms, or $R^{30}$ and $R^{31}$ taken together with the phosphoramidite nitrogen atom form a saturated nitrogen heterocycle; and $R^{32}$ is a phosphite ester protecting group which prevents unwanted extension of the oligonucleotide. Generally, $R^{32}$ is stable to oligonucleotide synthesis conditions yet is able to be removed from a synthetic oligonucleotide product with a reagent that does not adversely affect the integrity of the oligonucleotide or the dye. $R^{32}$ may be: (i) methyl, (ii) 2-cyanoethyl; —$CH_2CH_2CN$, or (iii) 2-(4-nitrophenyl)ethyl; —$CH_2CH_2$(p-$NO_2$Ph). Embodiments of phosphoramidite reagents include where: (i) $R^{30}$ and $R^{31}$ are each isopropyl, (ii) $R^{30}$ and $R^{31}$ taken together is morpholino, (iii) L is $C_1$–$C_{12}$ alkyl, (iv) $R^{32}$ is 2-cyanoethyl, and (v) DYE is attached at $R^{18}$ or $R^{19}$ by a linker. The linker, L, may alternatively be:

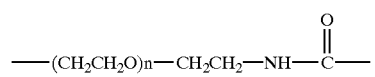

where n ranges from 1 to 10. An example of phosphoramidite reagent III has the structure:

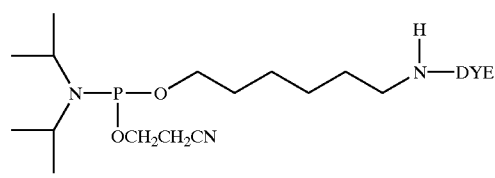

Phosphoramidite dye reagents III effect labelling of a substrate with a single, substantially pure, atropisomeric xanthene of the invention. Where the substrate is an oligonucleotide, the dye will be attached at the 5' terminus of the oligonucleotide, as a consequence of the typical 3' to 5' direction of synthesis, or at the 3' terminus of the oligonucleotide when the 5' to 3' direction synthesis method is practiced (Wagner (1997) Nucleosides & Nucleotides 16:1657–60). Reagent III may be coupled to a polynucleotide which is bound to a solid support, e.g. through the 3' terminus. Other phosphoramidite dye reagents, nucleosidic and non-nucleosidic allow for labelling at other sites of an oligonucleotide, e.g. 3' terminus, nucleobase, internucleotide linkage, sugar. Labelling at the nucleobase, internucleotide linkage, and sugar sites allows for internal and multiple labelling with fluorescent dyes.

An atropisomeric xanthene compound of the invention may be converted to a non-nucleosidic, phosphoramidite labelling reagent by any known method of phosphitylation of nucleophilic functionality with trivalent phosphitylating reagents. For example, when the xanthene contains a carboxyl group, e.g. $R^{19}$=$CO_2H$, the carboxyl may be activated, e.g. to the NHS, and amidated with 6-amino-1-hexanol. The resulting hydroxyl may be phosphitylated with bis (diisopropylamino)cyanoethylphosphite or chloro-diisopropylamino-cyanoethylphosphine to give the phosphoramidite dye-labelling reagent (Theisen (1992) "Fluorescent dye phosphoramidite labelling of oligonucleotides", in *Nucleic Acid Symposium Series* No. 27, Oxford University Press, Oxford, pp. 99–100). Alternatively, the carboxyl group of the compound may be reduced to the hydroxyl, to be phosphitylated.

The phosphoramidite reagent III reacts with a hydroxyl group, e.g. 5' terminal OH of an oligonucleotide bound to a solid support, under mild acid activation, to form an internucleotide phosphite group which is then oxidized to an internucleotide phosphate group. In some instances, the xanthene compound may contain functional groups, e.g. $Z^1$ and $Z^2$ oxygens as in structure I, that require protection either during the synthesis of the phosphoramidite reagent or during its subsequent use to label molecules such as oligonucleotides. The protecting group(s) used will depend upon the nature of the functional groups, and will be apparent to those having skill in the art (Greene, T. and Wuts, P. *Protective Groups in Organic Synthesis*, 2nd Ed., John Wiley & Sons, New York, 1991). Generally, the protecting groups used should be stable under the acidic conditions (e.g. trichloroacetic acid, dichloroacetic acid) commonly employed in oligonucleotide synthesis to remove 5'-hydroxyl protecting groups (e.g., dimethoxytrityl) and labile under the basic conditions (ammonium hydroxide, aqueous methylamine) used to deprotect and/or cleave synthetic oligonucleotides from solid supports.

Polypeptides, antibodies, and other biopolymers comprised of amino acids and amino acid analogs may be covalently labelled by conjugation with the atropisomeric xanthene compounds of the invention. Typically, the compound is in electrophilic form, e.g. NHS reactive linking group, which reacts with a nucleophilic group of the peptide, e.g. amino terminus, or amino side chain of an amino acid such as lysine. Alternatively, the dye may be in nucleophilic form, e.g. amino- or thiol-reactive linking group, which may react with an electrophilic group of the peptide, e.g. NHS of the carboxyl terminus or carboxyl side chain of an amino acid. Labelled polypeptides may retain their specific binding and recognition properties in interacting with cell surface and intracellular components. The xanthene compound, acting as a dye, provides a detection element for localizing, visualizing, and quantitating the binding or recognition event. Polypeptides can also be labelled with two moieties, a fluorescent reporter and quencher, which together undergo fluorescence resonance energy transfer (FRET). The fluorescent reporter may be partially or significantly quenched by the quencher moiety in an intact polypeptide. Upon cleavage of the polypeptide by a peptidase or protease, a detectable increase in fluorescence may be measured (Knight, C. (1995) "Fluorimetric Assays of Proteolytic Enzymes", Methods in Enzymology, Academic Press, 248:18–34).

Labelled Nucleotides

A preferred class of labelled substrates include conjugates of nucleosides and nucleotides that are labelled with the dyes of the invention. Such labelled nucleosides and nucleotides are particularly useful for labelling polynucleotides formed by enzymatic synthesis, e.g., labelled nucleotide 5'-triphosphates used in the context of PCR amplification, Sanger-type polynucleotide sequencing, and nick-translation reactions.

Nucleosides and nucleotides can be labelled at sites on the sugar or nucleobase moieties. Preferred nucleobase labelling sites include the 8-C of a purine nucleobase, the 7-C or 8-C of a 7-deazapurine nucleobase, and the 5-position of a pyrimidine nucleobase. Between a nucleoside or nucleotide and a dye, a linker may attach to an atropisomeric xanthene compound at any position.

The labelled nucleoside or nucleotide may be enzymatically incorporatable and enzymatically extendable. Nucleosides or nucleotides labelled with compounds of the invention may have formula IV:

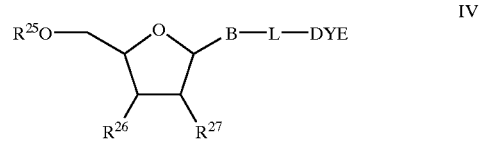

where DYE is a protected or unprotected form of compounds I or II, including energy-transfer dye. B may be any nucleobase, e.g. uracil, thymine, cytosine, adenine, 7-deazaadenine, guanine, and 8-deazaguanosine. $R^{25}$ is H, monophosphate, diphosphate, triphosphate, thiophosphate, or phosphate ester analog. $R^{26}$ and $R^{27}$, when taken alone, are each independently H, HO, F and a phosphoramidite. Where $R^{26}$ or $R^{27}$ is phosphoramidite, $R^{25}$ is an acid-cleavable hydroxyl protecting group, e.g. dimethoxytrityl, which allows subsequent monomer coupling under automated synthesis conditions (Caruthers, "Phosphoramidite compounds and processes", U.S. Pat. No. 4,415,732; Caruthers, "Process for preparing polynucleotides", U.S. Pat. No. 4,458,066; Beaucage, S. and Iyer, R. (1992) "Advances in the synthesis of oligonucleotides by the phosphoramidite approach", Tetrahedron 48:2223–2311).

Where the labelled nucleoside or nucleotide is a terminator, $R^{26}$ and $R^{27}$ are selected to block polymerase-mediated template-directed polymerization. In terminator nucleotides, $R^{26}$ and $R^{27}$, when taken alone, are each independently H, F, and a moiety which blocks polymerase-mediated template-directed polymerization, or when taken together form 2'-3'-didehydroribose. In formula IV, when both $R^{26}$ and $R^{27}$ are hydroxyl, the resultant compounds are labelled ribonucleosides and ribonucleotides (NTP). When $R^{27}$ is hydrogen and $R^{26}$ is hydroxyl, the resultant compounds are labelled 2'-deoxyribonucleosides and nucleotides (dNTP). When $R^{26}$ and $R^{27}$ are each hydrogen, the resultant compounds are 2',3'-dideoxyribonucleosides and nucleotides (ddNTP). Labelled ddNTP find particular use as terminators in Sanger-type DNA sequencing methods utilizing fluorescent detection. Labelled 2'-deoxyribonucleoside-5'-triphosphates (dNTP) find particular use as reagents for labelling DNA polymerase extension products, e.g., in the polymerase chain reaction or nick-translation. Labelled ribonucleoside-5'-triphosphates (NTP) find particular use as reagents for labelling RNA polymerase extension products.

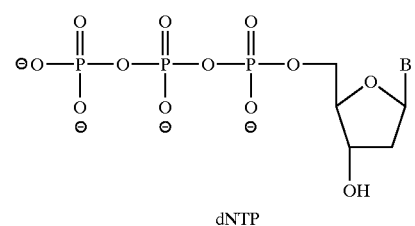

dNTP

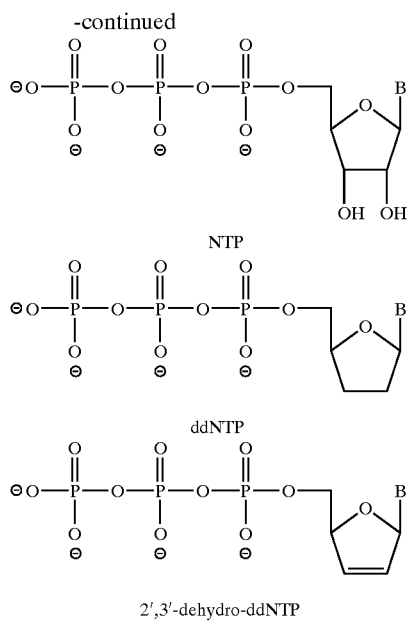

NTP ddNTP

2′,3′-dehydro-ddNTP

Alkynylamino-linked compounds IV, where L includes an alkyndiyl group, are useful for conjugating atropisomeric xanthene compounds to nucleosides, nucleotides and analogs therein. Their synthesis is taught in EP 87305844.0 and Hobbs, (1989) J. Org. Chem. 54:3420. The corresponding nucleoside mono-, di- and triphosphates are obtained by standard techniques (for example, the methods described in U.S. Pat. Nos. 5,821,356; 5,770,716; 5,948,648; 6,096,875). Methods for synthesizing compounds IV with modified propargylethoxyamido linkers L can also be found in these patents. Additional synthesis procedures suitable for use in synthesizing compounds according to structural formula IV are described, for example, in Gibson (1987) Nucl. Acids Res. 15:6455–6467; Gebeyehu (1987) Nucl. Acids Res. 15:4513–4535; Haralambidis (1987) Nucl. Acids Res. 15:4856–4876; Nelson (1986) Nucleosides and Nucleotides. 5(3):233–241; Bergstrom (1989) J. Am. Chem. Soc. 111:374–375; U.S. Pat. Nos. 4,855,225, 5,231,191 and 5,449,767, which are incorporated herein by reference. Any of these methods can be routinely adapted or modified as necessary to synthesize the full range of labelled nucleosides, nucleotides, and analogs described herein.

One embodiment of the alkynyl linker L may be:

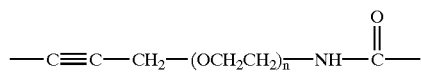

wherein n is 0, 1, or 2.

Energy-transfer dye pairs can be conjugated to a nucleotide 5′-triphosphate by linking through a nucleobase amino group to: (i) an activated ester of a energy-transfer dye pair, or (ii) stepwise coupling to one dye, e.g. R11-protected aminomethyl, $R^{18}$-carboxyl fluorescein, then coupling the unprotected $R^{11}$-aminomethyl to the second dye of the pair.

Linker reagents may be prepared by known synthetic methods. For example, phosphate linker reagent 5 is synthesized starting from the cyclic phosphoramidite 7. Phosphitylation of 7 with methyl glycolate 6 was followed by in situ oxidation to the pentavalent phosphate 8. Hydrolysis of the methyl ester, the trifluoroacetate group, and demethylation gave 9. Protection of the amino group with Fmoc gave 10 which was activated as the N-hydroxysuccinimide ester, linker reagent 5 (FIG. 4, Example 9).

Figure 6:
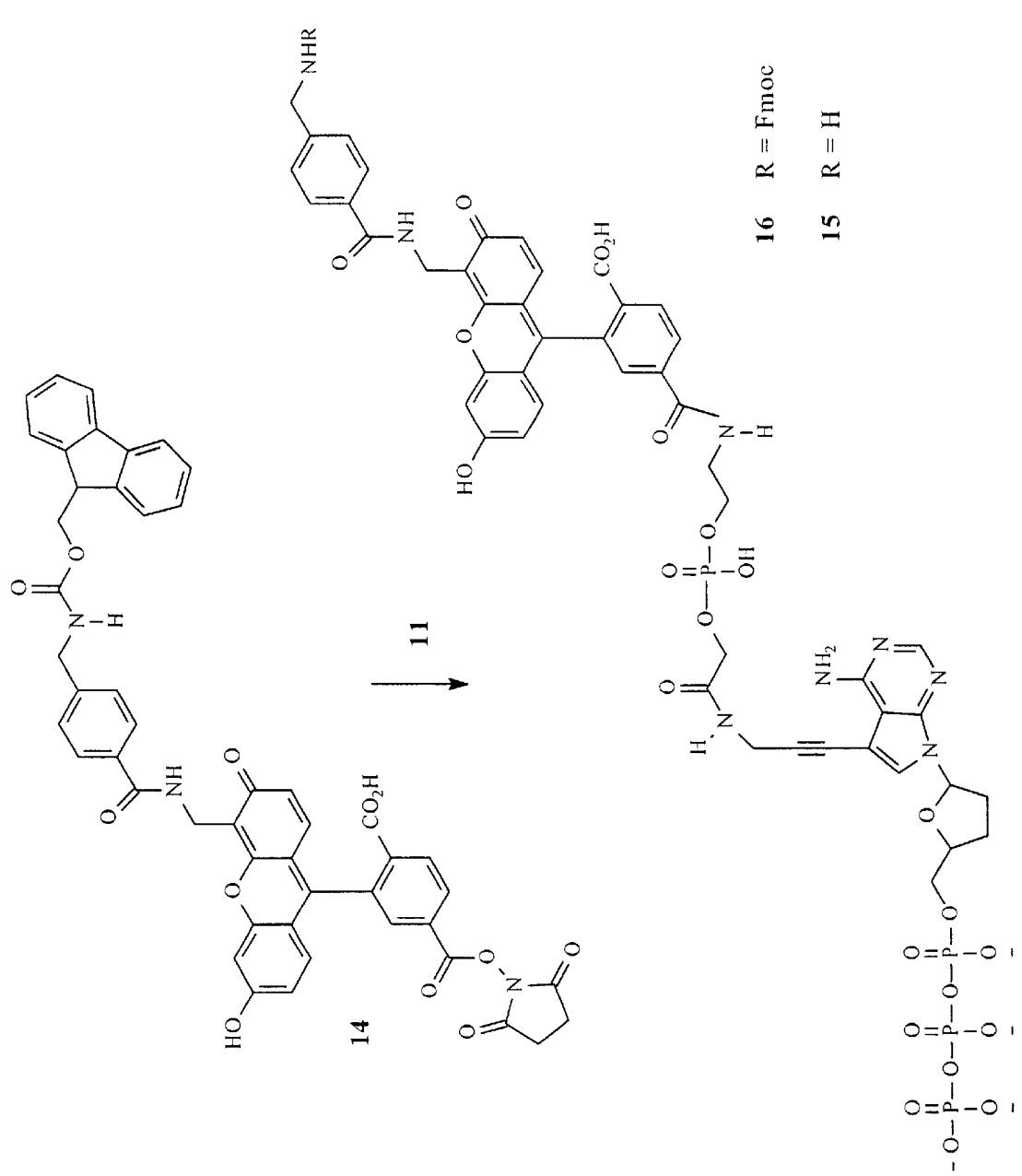
FIG. 6 shows the synthesis of aminomethyl-FAM-propargylphosphorylamino-ddATP 15.

An alkynylamino-linked nucleotide can be prepared by first coupling NHS linker reagent 5 with 7-deaza-7-propargylamino-ddATP 12 to give 13, followed by hydrolysis of the Fmoc group to give 11 (FIG. 5, Example 10). The amino atropisomeric xanthene 1a is coupled with the N-Fmoc, NHS ester of p-aminomethylbenzoic acid (Example 11) and then activated as the NHS ester to give 14 (FIG. 6). Reaction of 11 and 14 gave the atropisomeric xanthene ddATP compound 16. The Fmoc group was removed with ammonium hydroxide to give 15 (FIG. 6, Example 12).

Figure 7:
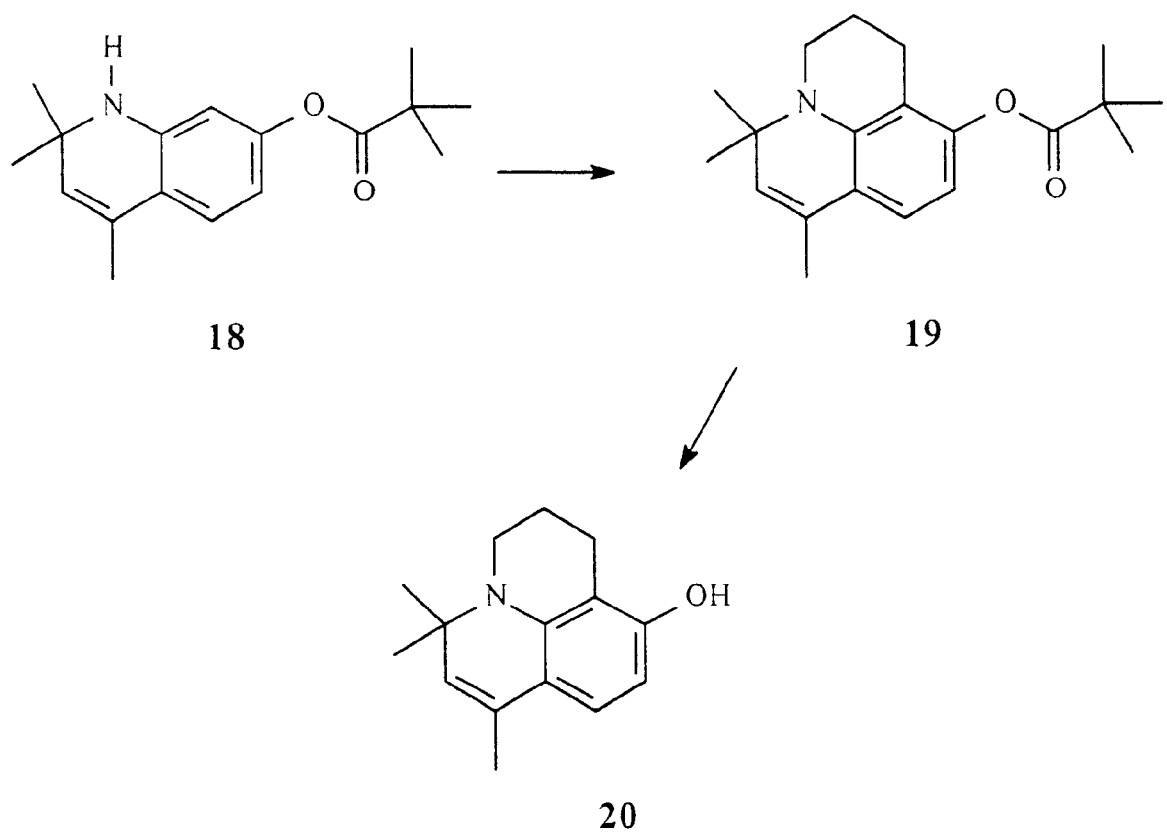
FIG. 7 shows the synthesis of tricyclic amine 20.
Figure 8:
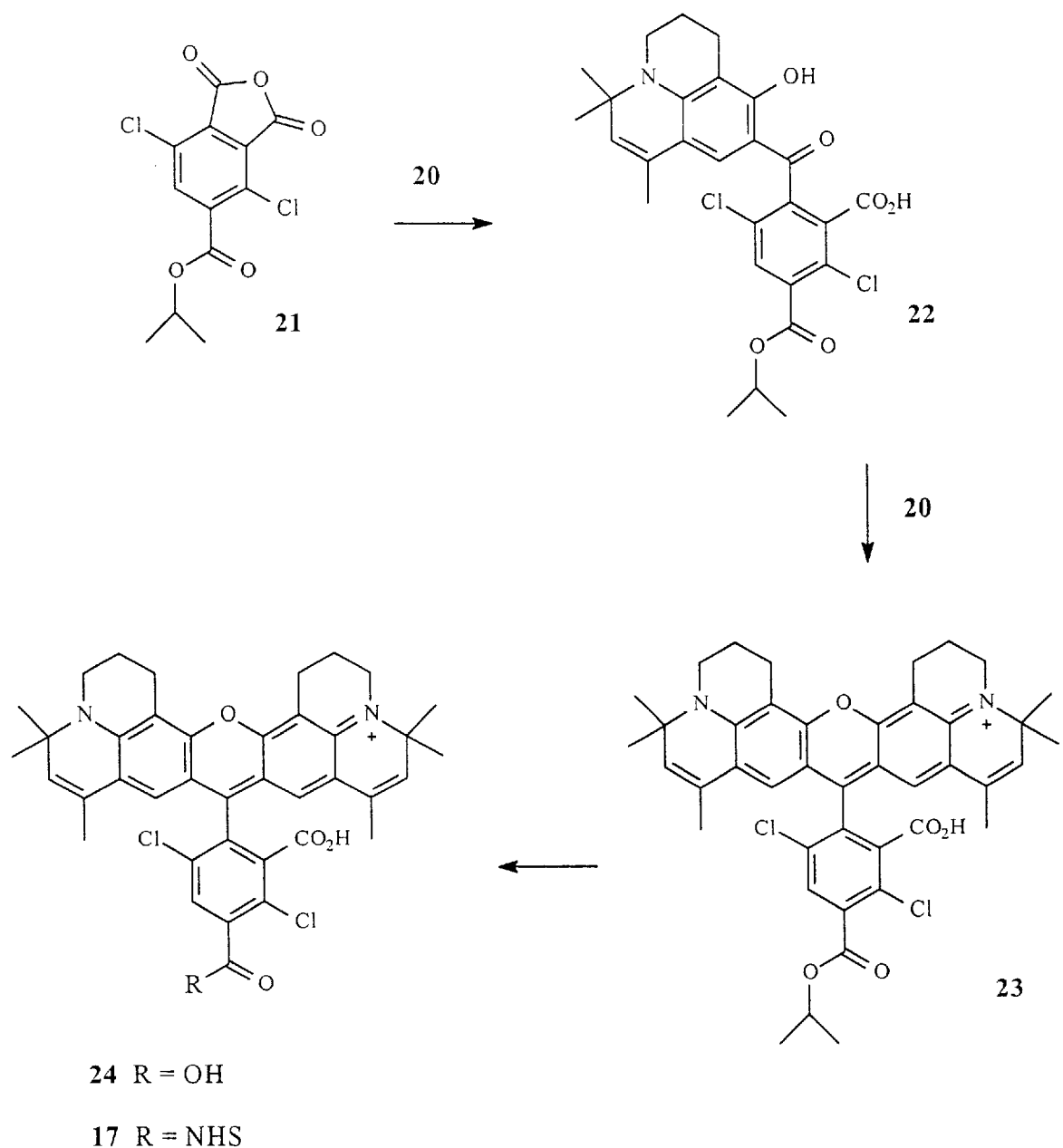
FIG. 8 shows the synthesis of NHS-rhodamine dye 17.

The NHS-rhodamine dye 17 was synthesized from bicyclic amine 18. Cyclization with 1-bromo-3-chloropropane gave tricyclic ester 19, which was hydrolyzed to tricyclic amine 20 (FIG. 7, Example 13). Friedel-Crafts acylation of 20 with anhydride 21 gave the ketone 22 which was reacted with another equivalent of 20 to give symmetric rhodamine isopropyl ester 23. The ester of 23 was cleaved and the carboxylic acid 24 was converted to NHS-rhodamine dye 17 (FIG. 8, Example 13).

Figure 9:
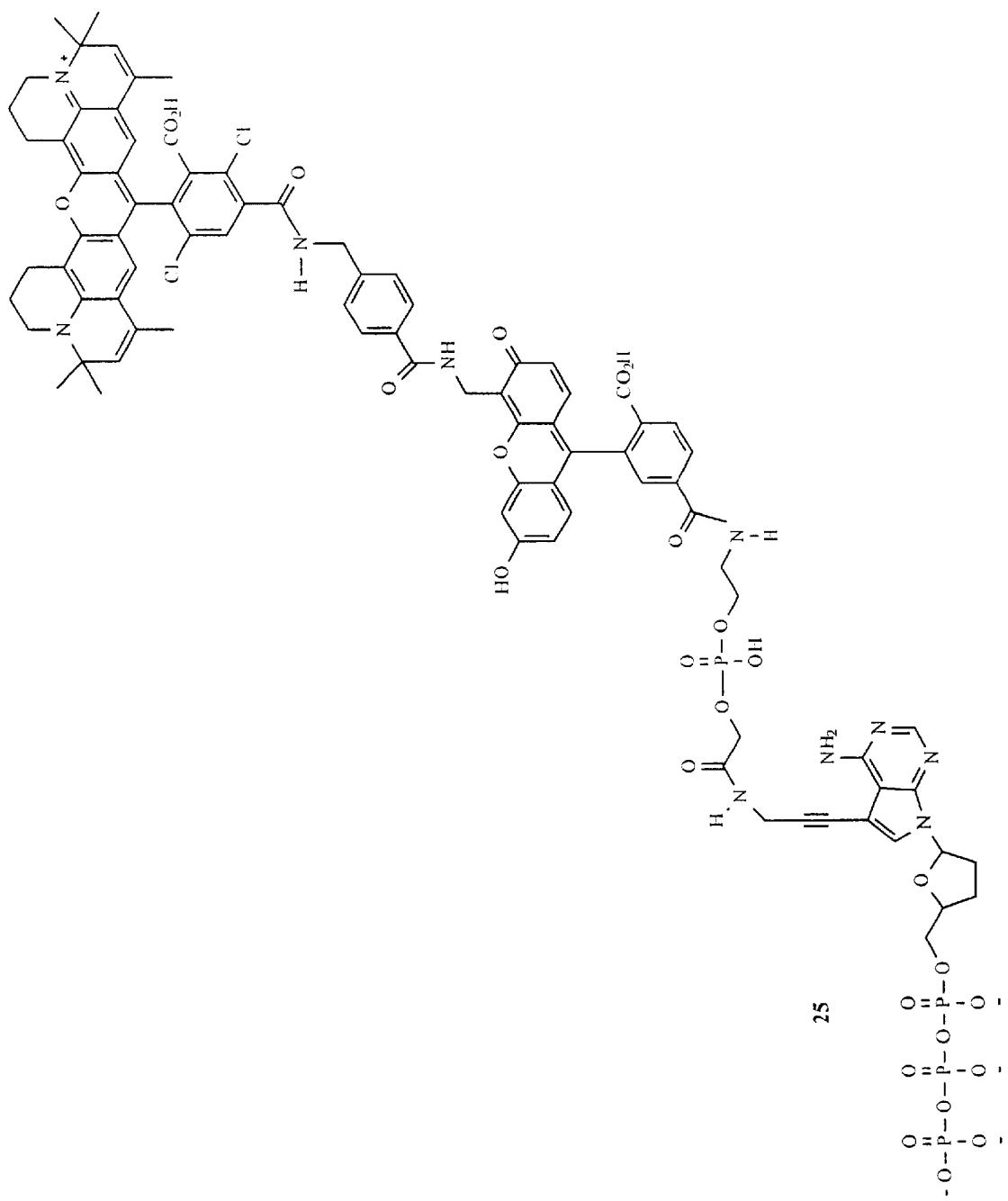
FIG. 9 shows the structure of energy-transfer ddATP terminator 25.

The substantially pure atropisomer xanthene energy transfer ddATP terminator 25 was formed by coupling 15 with 17, followed by anion-exchange HPLC purification (FIG. 9, Example 14).

Alternative synthetic routes to energy-transfer nucleotides and polynucleotides, with different convergent schemes may be practiced. The substrate, dye, and linker subunits, or synthons, may be assembled for coupling in any order. For example, the energy-transfer pair of donor dye and acceptor dye may be covalently attached through a linker and then coupled to the nucleotide or polynucleotide. Many different synthetic routes can be practiced which result in the labelling of nucleotides with the dyes of the invention. Reactive functionality, such as carboxylic acid, amino, hydroxyl groups, may require protection, utilizing the vast art of organic synthesis methodology.

Figure 10:
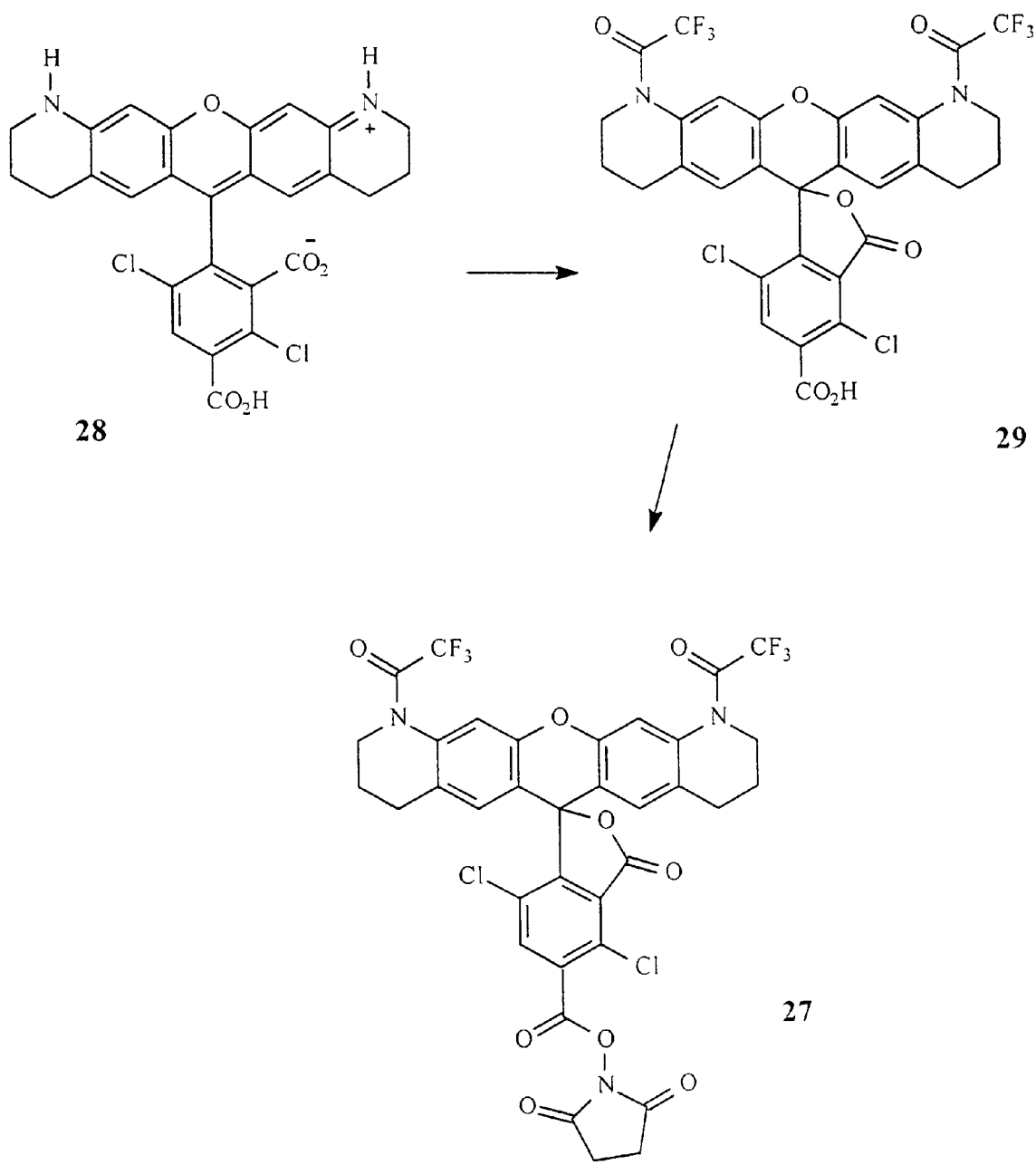
FIG. 10 shows the synthesis of bis-trifluoroacetamide rhodamine NHS 27.
Figure 11:
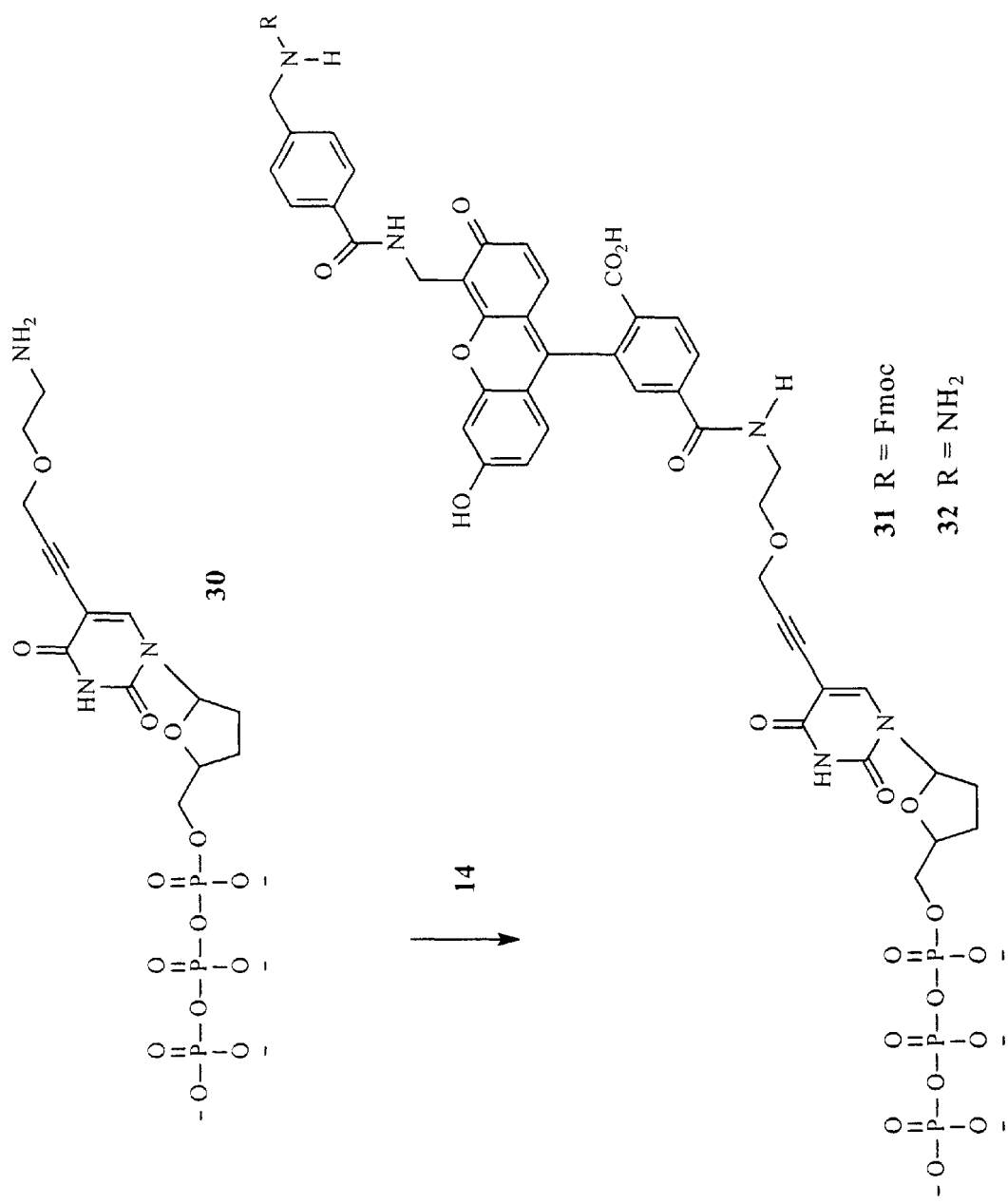
FIG. 11 shows the synthesis of aminomethylbenzamide-aminomethyl-FAM-propargylethoxyamino-ddTTP 32.
Figure 12:
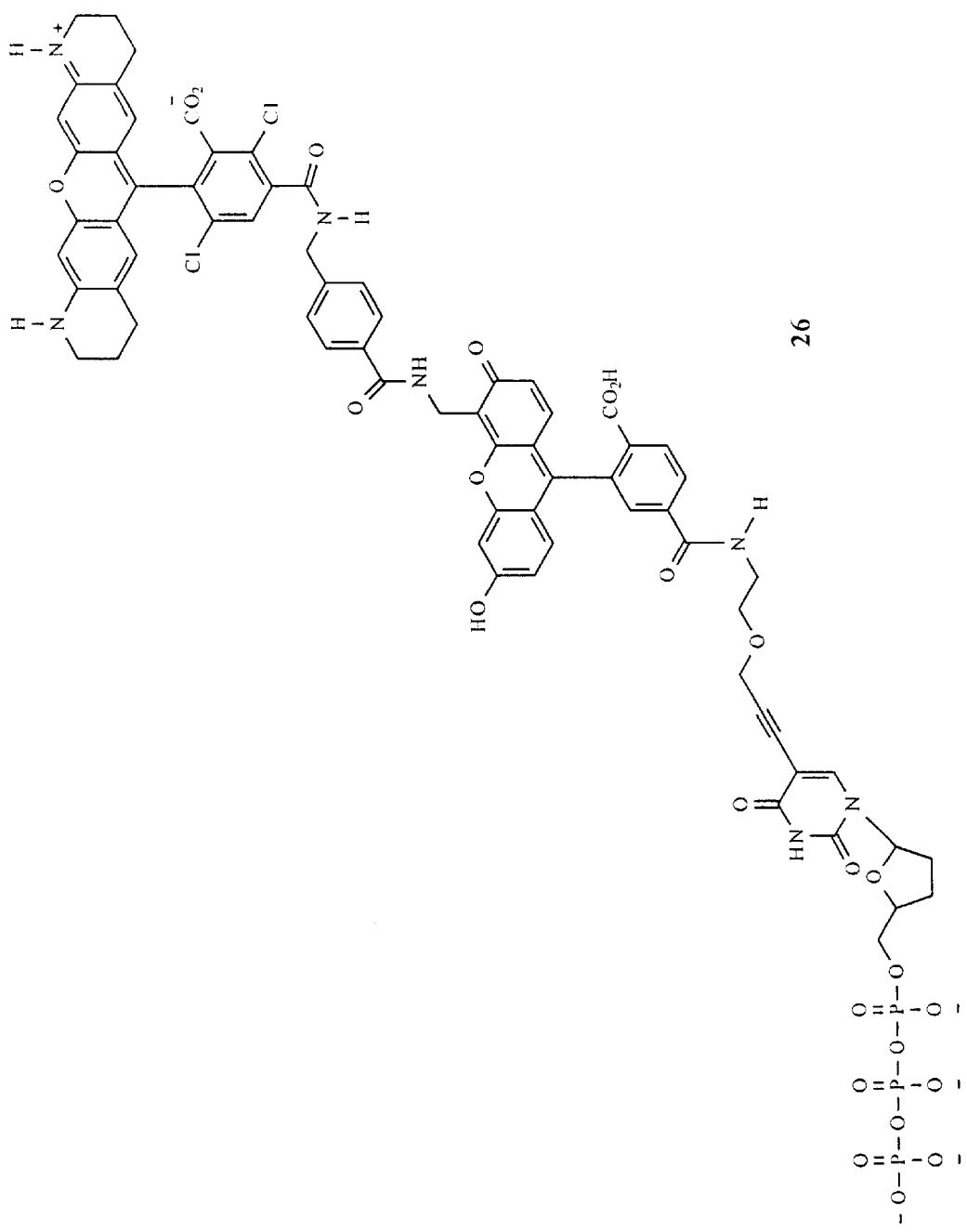
FIG. 12 shows the structure of energy-transfer ddTTP terminator 26.

Another rhodamine dye 28 was protected as the bis-trifluoroacetamide 29 and converted to the NHS compound 27 (FIG. 10, Example 15). Propargylethoxyamino ddTTP 30 was coupled with atropisomer xanthene compound 14 to give Fmoc atropisomer xanthene ddTTP 31 which was hydrolyzed to 32 (FIG. 11, Example 16). Reaction of 27 and 32 gave atropisomer, energy-transfer terminator ddTTP 26, purified by anion-exchange HPLC (FIG. 12, Example 17).

Labelled Oligonucleotides

Oligonucleotides are commonly synthesized on solid supports by the phosphoramidite method (U.S. Pat. Nos. 4,415,732; 4,973,679; 4,458,066; Beaucage, S. and Iyer, R. (1992) Tetrahedron 48:2223–2311) using commercially available phosphoramidite nucleosides, supports e.g. silica, controlled-pore-glass (U.S. Pat. No. 4,458,066) and polystyrene (U.S. Pat. Nos. 5,047,524 and 5,262,530) and automated synthesizers (Models 392, 394, 3948 DNA/RNA Synthesizers, Applied Biosystems).

Another preferred class of labelled substrates include conjugates of oligonucleotides and the compounds of the invention. Such conjugates may find utility as DNA sequencing primers, PCR primers, oligonucleotide hybridization probes, oligonucleotide ligation probes, double-labelled 5′-exonuclease (TaqMan™) probes, and the like (Fung, U.S. Pat. No. 4,757,141; Andrus, "Chemical methods for 5′ non-isotopic labelling of PCR probes and primers" (1995) in *PCR 2: A Practical Approach*, Oxford University Press, Oxford, pp. 39–54; Hermanson, *Bioconjugate Techniques*, (1996) cademic Press, San Diego, Calif. pp. 40–55, 643–71; Mullah (1998) "Efficient synthesis of double dye-labelled oligodeoxyribonucleotide probes and their application in a real time PCR assay", Nucl. Acids Res. 26:1026–1031). A labelled oligonucleotide may have formula V:

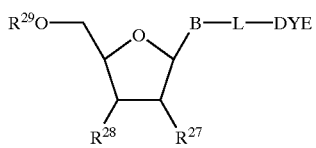

where the oligonucleotide comprises 2 to 100 nucleotides. DYE is a protected or unprotected form of compounds I or II, including energy-transfer dye. B is any nucleobase, e.g. uracil, thymine, cytosine, adenine, 7-deazaadenine, guanine, and 8-deazaguanosine. L is a linker. $R^{27}$ is H, OH, halide, azide, amine, $C_1$–$C_6$ aminoalkyl, $C_1$–$C_6$ alkyl, allyl, $C_1$–$C_6$ alkoxy, $OCH_3$, or $OCH_2CH$=$CH_2$. $R^{22}$ is H, phosphate, internucleotide phosphodiester, or internucleotide analog. $R^{29}$ is H, phosphate, internucleotide phosphodiester, or internucleotide analog. In this embodiment, structure V, the nucleobase-labelled oligonucleotide may bear multiple dyes of the invention attached through the nucleobases. Nucleobase-labelled oligonucleotide V may be formed by: (i) enzymatic incorporation of enzymatically incorporatable nucleotide reagents IV where $R^{25}$ is triphosphate, by a DNA polymerase or ligase, and (ii) coupling of a nucleoside phosphoramidite reagent by automated synthesis. Whereas, nucleobase-labelled oligonucleotides V may be multiply labelled by incorporation of more than one incorporatable nucleotide IV, labelling with a dye label reagent such as III leads to singly 5'-labelled oligonucleotides, according to formula VI:

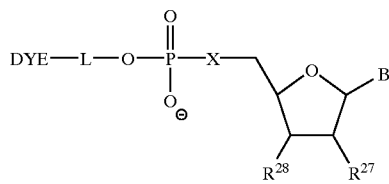

where X is O, NH, or S; $R^{27}$ is H, OH, halide, azide, amine, $C_1$–$C_6$ aminoalkyl, $C_1$–$C_6$ alkyl, allyl, $C_1$–$C_6$ alkoxy, $OCH_3$, or $OCH_2CH$=$CH_2$; $R^{28}$ is H, phosphate, internucleotide phosphodiester, or internucleotide analog; and L is $C_1$–$C_{12}$ alkyl, aryl, or polyethyleneoxy of up to 100 ethyleneoxy units.

The linker L in formulas V or VI may be attached at any site on the atropisomeric xanthene compound of the invention, DYE, including $R^1$, $R^{11}$, $R^{18}$, $R^{19}$, $Z^1$ and $Z^2$ of structure I.

In a first method for labelling synthetic oligonucleotides, a nucleophilic functionality, e.g. a primary aliphatic amine, is introduced at a labelling attachment site on an oligonucleotide, e.g. a 5' terminus. After automated, solid-support synthesis is complete, the oligonucleotide is cleaved from the support and all protecting groups are removed. The nucleophile-oligonucleotide is reacted with an excess of a label reagent containing an electrophilic moiety, e.g. isothiocyanate or activated ester, e.g. N-hydroxysuccinimide (NHS), under homogeneous solution conditions (Hermanson, Bioconjugate Techniques, (1996) Academic Press, San Diego, Calif. pp. 40–55, 643–71; Andrus, A. "Chemical methods for 5' non-isotopic labelling of PCR probes and primers" (1995) in PCR 2: A Practical Approach, Oxford University Press, Oxford, pp. 39–54). Labelled oligonucleotides VI may be formed by reacting a reactive linking group form, e.g. NHS, of a dye, with a 5'-aminoalkyl oligonucleotide.

In a second method, a label is directly incorporated into the oligonucleotide during or prior to automated synthesis, for example as a support reagent (Mullah, "Solid support reagents for the direct synthesis of 3'-labelled polynucleotides", U.S. Pat. No. 5,736,626; Nelson, "Multifunctional controlled pore glass reagent for solid phase oligonucleotide synthesis", U.S. Pat. No. 5,141,813) or as a phosphoramidite reagent III. Certain fluorescent dyes and other labels have been functionalized as phosphoramidite reagents for 5' labelling (Theisen (1992) Nucleic Acid Symposium Series No. 27, Oxford University Press, Oxford, pp. 99–100).

Generally, if the labelled oligonucleotide is made by enzymatic synthesis, the following procedure may be used. A target DNA is denatured and an oligonucleotide primer is annealed to the template DNA. A mixture of enzymatically-incorporatable nucleotides or nucleotide analogs capable of supporting continuous template-directed enzymatic extension of the primed target (e.g., a mixture including dGTP, dATP, dCTP and dTTP or dUTP) is added to the primed target. At least a fraction of the nucleotides are labelled terminators IV, labelled with an atropisomer xanthene dye II. A polymerase enzyme is next added to the mixture under conditions where the polymerase enzyme is active. A labelled oligonucleotide is formed by the incorporation of the labelled nucleotides or terminators during polymerase-mediated strand synthesis. In an alternative enzymatic synthesis method, two primers are used instead of one: one complementary to the (+) strand of the target and another complementary to the (–) strand of the target, the polymerase is a thermostable polymerase and the reaction temperature is cycled between a denaturation temperature and an extension temperature, thereby exponentially synthesizing a labelled complement to the target sequence by PCR (Innis (1990) PCR Protocols, Eds., Academic Press).

In one preferred post-synthesis chemical labelling method an oligonucleotide is labelled as follows. An NHS form of a dye according to structure I is dissolved or suspended in DMSO and added in excess (5–20 equivalents) to a 5'-aminohexyl oligonucleotide in 0.25 M bicarbonate/carbonate buffer at about pH 9 and allowed to react for 6 hours, e.g., U.S. Pat. No. 4,757,141. The atropisomer xanthene labelled oligonucleotide can be separated from unreacted dye by passage through a size-exclusion chromatography column eluting with buffer, e.g., 0.1 molar triethylamine acetate (TEAA). The fraction containing the crude labelled oligonucleotide is further purified by reverse phase HPLC employing gradient elution.

Polynucleotides labelled with the atropisomer xanthene compounds of the present invention may be additionally labelled with moieties that affect the rate of electrophoretic migration, i.e. mobility-modifying labels. Mobility-modifying labels include polyethyleneoxy units, —$(CH_2CH_2)_n$— where n may be 1 to 100 (Grossman, U.S. Pat. No. 5,624,800). Preferably, n is from 2 to 20. The polyethyleneoxy units may be interspersed with phosphate groups. Specifically labelling atropisomer xanthene-labelled polynucleotides with additional labels of polyethyleneoxy of discrete and known size allows for separation by electrophoresis, substantially independent of the number of nucleotides in the polynucleotide. That is, polynucleotides of the same length may be discriminated upon by the presence of spectrally resolvable dye labels and mobility-modifying labels. Polynucleotides bearing both dye labels and mobility-modifying labels may be formed enzymatically by ligation or polymerase extension of the single-labelled polynucleotide or nucleotide constituents.

Methods

Methods requiring simultaneous detection of multiple spatially-overlapping analytes may benefit from substantially pure atropisomers of asymmetric xanthene dyes as labels. The atropisomer xanthene compounds of the present invention are well suited for any method utilizing fluorescent detection, such as polymerase chain reaction (PCR) amplification, DNA sequencing, antisense transcriptional and translational control of gene expression, genetic analysis, and DNA probe-based diagnostic testing (Kricka, L. (1992) *Nonisotopic DNA Probe Techniques,* Academic Press, San Diego, pp.3–28). Fluorescence detection of fluorescent dye-labelled oligonucleotides is the basis for nucleic acid sequence detection assays such as 5' exonuclease assay (Livak, U.S. Pat. No. 5,723,591), FRET hybridization (Tyagi, S. and Kramer, F. (1996) "Molecular Beacons: Probes that fluoresce upon hybridization", Nature Biotechnology, 14:303–08), genetic linkage mapping (Dib (1996) "A comprehensive genetic map of the human genome based on 5,264 microsatellites", Nature 380:152–54) and oligonucleotide-ligation assay (Grossman (1994) "High-density multiplex detection of nucleic acid sequences: oligonucleotide ligation assay and sequence-coded separation", Nucl. Acids Res. 22:4527–34).

The present invention is particularly well suited for detecting classes of differently-labelled polynucleotides that have been subjected to a biochemical separation procedure, such as electrophoresis (Rickwood and Hames, Eds., *Gel Electrophoresis of Nucleic Acids: A Practical Approach,* IRL Press Limited, London, 1981). The electrophoretic matrix may be a sieving polymer, e.g. crosslinked or uncrosslinked polyacrylamide, or other amide-containing polymer, having a concentration (weight to volume) of between about 2–20 weight percent (Madabhushi, U.S. Pat. Nos. 5,552,028; 5,567,292; 5,916,426). The electrophoretic matrix maybe configured in a slab gel or capillary format (Rosenblum, (1997) Nucleic Acids Res. 25:3925–29; Mathies, U.S. Pat. No. 5,274,240).

Primer Extension

In a preferred category of methods referred to herein as "fragment analysis" or "genetic analysis" methods, polynucleotide fragments labelled with fluorescent dyes, including substantially pure atropisomeric xanthene compounds, are generated through template-directed enzymatic synthesis using labelled primers or nucleotides, e.g. by ligation or polymerase-directed primer extension. The polynucleotide fragments may be subjected to a size-dependent separation process, e.g., electrophoresis or chromatography, and the separated fragments are detected subsequent to the separation, e.g., by laser-induced fluorescence (Hunkapiller, U.S. Pat. No. 4,811,218). Multiple classes of polynucleotides may be separated simultaneously and the different classes are distinguished by spectrally resolvable labels, including dyes of the invention. In electrophoresis, the classes separate on the basis of electrophoretic migration rate.

DNA Sequencing

Preferably, the chain termination methods of DNA sequencing, i.e. dideoxy DNA sequencing, or Sanger-type sequencing, and fragment analysis is employed (Sanger (1977) "DNA sequencing with chain-terminating inhibitors", Proc. Natl. Acad. Sci. USA 74:5463–5467). Exemplary chain-terminating nucleotide analogs include the 2',3'-dideoxynucleoside 5'-triphosphates (ddNTP) which lack the 3'-OH group necessary for 3' to 5' DNA chain elongation. Primers or ddNTP may be labelled with the substantially pure atropisomer xanthene dyes of the invention and detected by fluorescence after separation of the fragments by high-resolution electrophoresis. Dyes can be linked to functionality on the 5' terminus of the primer, e.g. amino (Fung, U.S. Pat. No. 4,757,141), on the nucleobase of a primer; or on the nucleobase of a dideoxynucleotide, e.g. via alkynylamino linking groups (Khan, U.S. Pat. Nos. 5,770,716; and 5,821,356; Hobbs, U.S. Pat. No. 5,151,507).

Each of the terminators bears a different fluorescent dye and collectively the terminators of the experiment bear a set of dyes including one or more from the dyes of the invention. In a preferred fragment analysis method, fragments labelled with dyes are identified by relative size, i.e. sequence length. Correspondence between fragment size and sequence is established by incorporation of the four possible terminating nucleotides ("terminators") and the members of a set of spectrally resolvable dyes (Bergot, U.S. Pat. No. 5,366,860). The set of spectrally resolvable dyes may include at least one substantially pure atropisomeric xanthene compound.

Ligation

The covalent joining of nucleic acid probes by ligase enzymes is one of the most useful tools available to molecular biologists. When two probes are annealed to a template nucleic acid where the two probes are adjacent and without intervening gaps, a phosphodiester bond can be formed between a 5' terminus of one probe and the 3' terminus of the other probe by a ligase enzyme, (Whiteley, U.S. Pat. No. 4,883,750; Landegren, (1988) "A ligase mediated gene detection technique", Science 241:1077–80; Nickerson, "Automated DNA diagnostics using an ELISA-based oligonucleotide assay" (1990) Proc. Natl. Acad. Sci USA 87:8923–27). Oligonucleotide ligation assays detect the presence of specific sequences in target DNA sample. Where one or both probes are labelled with a dye, the ligation product may be detected by fluorescence. One or both probes may be labelled with a substantially pure atropisomeric xanthene dye. Ligation products may be detected by electrophoresis, chromatography, or other size- or charge-based separation method.

Amplification

The atropisomer xanthene compounds of the invention find applications as labels on 5'-labelled oligonucleotide primers for the polymerase chain reaction (PCR) and other nucleic acid amplification and selection methods. PCR applications include the use of labelled oligonucleotides for genotyping by variable number tandem repeat (VNTR), short tandem repeat (STR), and microsatellite methods of amplification of repeat regions of double-stranded DNA that contain adjacent multiple copies of a particular sequence, with the number of repeating units being variable. Preferably, in such PCR genotyping methods, the PCR primer is labelled with an atropisomer xanthene of the invention.

In a particularly preferred embodiment, atropisomer xanthene compounds may be used in quantitative methods and reagents that provide real time or end-point measurements of amplification products during PCR (U.S. Pat. Nos. 5,210,015; 5,538,848). The exonuclease assay (Taqman®) employing fluorescent dye-quencher probes (U.S. Pat. No. 5,723,591; Mullah, (1998) "Efficient synthesis of double dye-labelled oligodeoxyribonucleotide probes and their application in a real time PCR assay", Nucl. Acids Res. 26:1026–1031) gives direct detection of polymerase chain reaction (PCR) products in a closed-tube system, with no sample processing beyond that required to perform the PCR. In the Taqman assay, the polymerase that conducts primer extension and amplifies the polynucleotide also displaces and cleaves a probe annealed to target sequence by 5' to 3' exonuclease activity. In a Taqman-type assay, the probe is self-quenching, labelled with fluorescent dye and quencher moieties, either of which may be dyes of the invention. Spectral overlap allows for efficient energy transfer (FRET) when the probe is intact (Clegg, (1992) "Fluorescence resonance energy transfer and nucleic acids", Meth. Enzymol. 211:353–388). When hybridized to a target sequence, the probe is cleaved during PCR to release a fluorescent signal that is proportional to the amount of target-probe hybrid present (U.S. Pat. Nos. 5,538,848; 5,723,591).

The progress of amplification can be monitored continuously, i.e. real-time detection. Spectrally-resolvable atropisomer xanthene dyes of the invention are useful in genotyping experiments after PCR amplification of target. In particular, a set of primer oligonucleotides, labelled at the 5' terminus, each with different dyes, can amplify multiple loci and discriminate single nucleotide polymorphisms (SNP) and alleles. Electrophoretic separation of the dye-labelled amplification products, with size standards, establishes a profile or characteristic data set indicating a certain genotype dependent on the set of primer sequences.

Hybridization Assays

Certain fluorescent dye-quencher probes which hybridize to target nucleic acids are useful in hybridization assays. When the probe is not hybridized to target, the probe may attain conformations that allow spatial proximity between the fluorescent dye and the quencher moieties resulting in fluorescence quenching. Upon hybridization to target, the moieties are physically separated, quenching ceases or diminishes, and fluorescence increases. Where the fluorescence is detectable or quantitated, the presence of target sequence in the sample is deduced. The atropisomeric dyes of the invention can also be employed as the fluorescent dye or the quencher moiety. Fluorescent dye-quencher probes with self-complementary sequences that form a "hairpin" region, so called "Molecular beacons" (Tyagi and Kramer) undergo the fluorescent change upon hybridization to their complementary target sequence, e.g. in situ quantitation of mRNA in living cells. Hybridization probes labelled with different fluorescent dyes, including the atropisomeric dyes of the invention, enable multiplex, homogeneous hybridization assays to be carried out in sealed reaction tubes.

Chromatography

The aforementioned methods employing substrates labelled with substantially pure atropisomer xanthene compounds may also be conducted where the labelled substrates are detected by chromatography (*HPLC of Macromolecules, A Practical Approach,* Second Edition, R. W. A. Oliver, Ed. (1997) Oxford University Press). The well established techniques of HPLC enable the separation of large substrates such as polynucleotides under reverse phase conditions where the sample substrate is dissolved and eluted in aqueous organic mobile phase from sorptive ion-exchange or hydrophobic interactions with an immobilized solid phase. When a chiral substrate such as a polynucleotide, polypeptide, or polysaccharide is labelled with a racemic mixture of atropisomeric xanthene compounds, diastereomers result. Essentially a redundant set of analytes are created which may obscure the analytical result. Analysis of the resulting diastereomeric mixture may lead to double peaks, broad peaks, and other limiting artifacts under the high-resolution conditions of HPLC. This problem is especially exacerbated where the chiral substrate is a mixture of closely related compounds, such as the nested set of polynucleotide fragments generated by the Sanger sequencing method. Use of a substantially pure atropisomeric form of xanthene compounds as labels for chiral substrates prevents this unwanted hindrance to analysis by removing one of the diastereomers. The surprising and unexpected benefit of the invention may be exemplified by sharper peaks, less split peaks, and better resolution in general.

Kits

The invention includes kits comprising the substantially pure atropisomer xanthene compounds of the invention and/or their labelled conjugates. In one embodiment, the kits are useful for conjugating an atropisomer xanthene compound with a linking moiety to another molecule, i.e. a substrate. Such kits generally comprise an atropisomer xanthene of the invention including an optional linking moiety and reagents, enzymes, buffers, solvents, etc. suitable for conjugating the dye to another molecule or substance. The atropisomer xanthene may be an acceptor or donor of an energy-transfer dye.

In one embodiment, the kits are useful for labelling enzymatically synthesized oligonucleotides and polynucleotides with the atropisomer xanthenes of the invention. Such kits generally comprise a labelled enzymatically-incorporatable nucleotide or nucleotide analog according to the invention, a mixture of enzymatically-incorporatable nucleotides or nucleotide analogs capable of supporting continuous primer extension and a polymerase enzyme. Preferably, the labelled enzymatically-incorporatable nucleotide or nucleotide analog is a compound according to structure IV, most preferably a labelled terminator. Preferred polymerases are thermostable, such as AMPLITAQ® DNA polymerase FS (Applied Biosystems, Foster City, Calif.).

Alternatively, the kit may include one or more primers. The primers may be labelled with atropisomer xanthenes and energy-transfer dyes including atropisomer xanthenes.

EXAMPLES

The invention will be further clarified by a consideration of the following examples, which are intended to be purely exemplary of the present invention and not to in any way limit its scope.

Example 1

Preparation of Menthyl Carbamate Diastereomers of C-1 Aminomethyl, C-19 Carboxy Fluorescein, 1a and 1b The hydrochloride salt of C-1 aminomethyl, C-19 carboxy fluorescein (5.16 gm, 11.6 mMol, 441.8 MW; Shipchandler (1987) Anal. Biochem. 162:89–101) was dissolved in 50 ml of deionized formamide and 10.2 ml diisopropylethylamine. (−) Menthyl chloroformate (3.06 gm, 3.0 ml, 14 mMol, 219 MW; Aldrich Chemical, Milwaukee, Wis.; Jour. Chem. Soc., Chem. Commun. (1987) 470; Yodo (1988) Chem. Pharm. Bull. 36:902) was added dropwise with stirring at room temperature under argon. After 1.5 hours, TLC analysis (ethyl acetate/hexane: 4/1) showed partial conversion of reactant to a higher Rf spot. Another 1 ml (−) Menthyl chloroformate was added and stirring was continued for another 0.5 hour. TLC analysis showed complete conversion to the higher Rf product. Dilution of the reaction mixture with saturated aqueous $NaHCO_3$ was followed by extraction with 500 ml ethyl acetate. The aqueous fraction was acidified to pH 3 and extracted with ethyl acetate. The combined organic fractions were dried over $Na_2SO_4$, filtered and concentrated under vacuum to give 4.5 gm, 66% yield of a mixture of 1a and 1b as a yellow powder (FIG. 1a).

Example 2
Separation and Isolation of Diastereomers 1a and 1b by HPLC

Crude diastereomers 1a and 1b were separated and purified by a two stage chromatography process on an open column, flash reverse phase column rough separation, followed by preparative reverse phase HPLC.

The mixture of 1a and 1b was dissolved in ethyl acetate and adsorbed on C-18 reverse phase silica gel. The solvent was removed under vacuum and the solid was loaded on the top of a pre-equilibrated C-18 reverse phase column (21 cm length×6 cm diameter). The diastereomers were separated and eluted with 25% $CH_3CN$ in 100 mM TEAA (triethylammonium acetate) by collecting fractions. The fractions were analyzed by analytical reverse phase HPLC on a C-18 column (Metachem ODS3, 25 cm length×4.6 mm inner diameter) with a linear gradient of 25% to 35% $CH_3CN$ in 100 mM TEAA from 0 to 30 minutes at 1.0 ml/min flow rate and 260 nm UV detection. The fractions that contained the first eluting diastereomer of at least 75% purity were combined and concentrated under vacuum to an orange oil. The first eluting diastereomer was arbitrarily assigned structure 1a. The fractions that contained the second eluting diastereomer of at least 75% purity were combined and concentrated under vacuum to an orange oil. The second eluting diastereomer was arbitrarily assigned structure 1b.

Figure 1B:
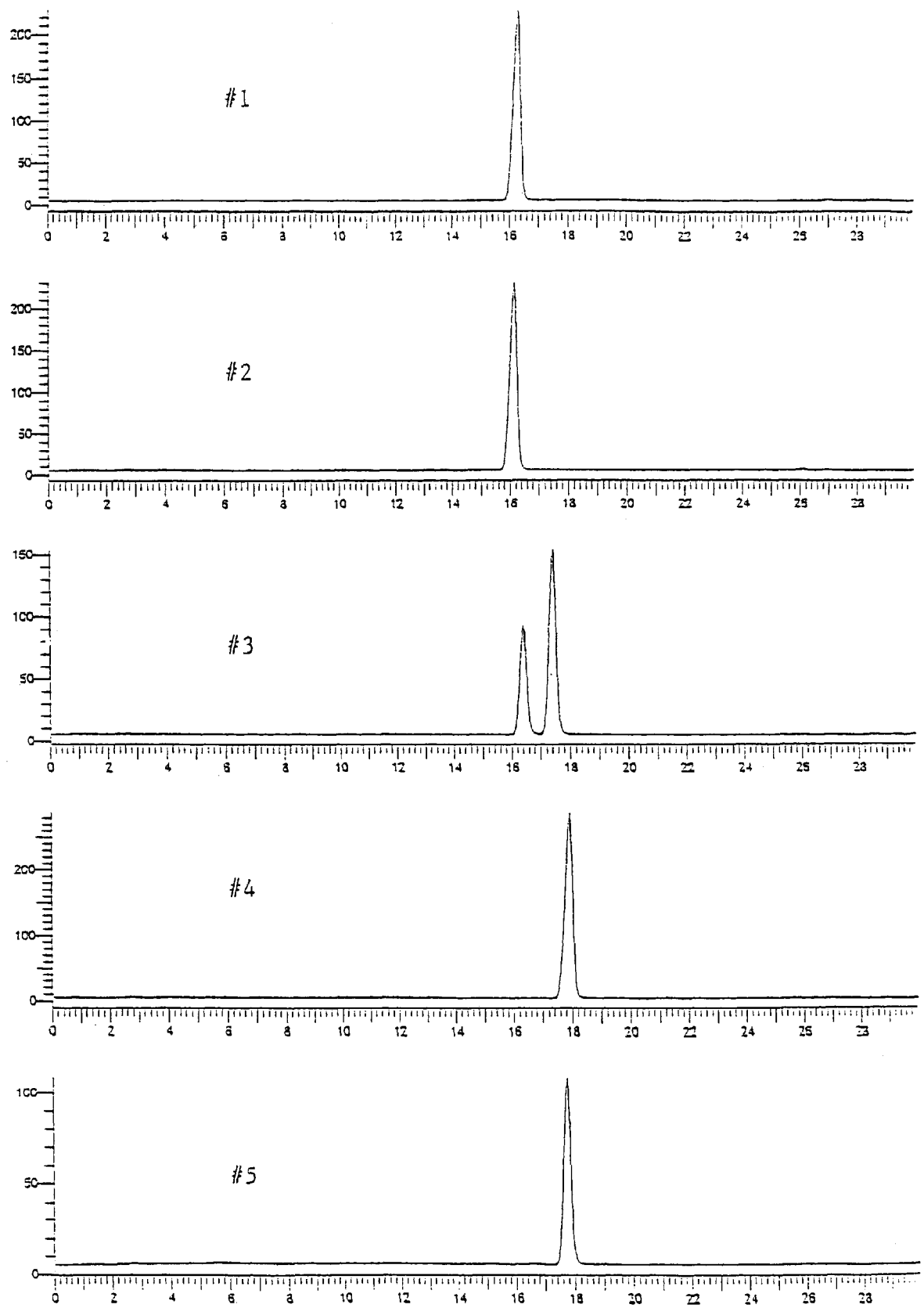
FIG. 1b shows reverse phase HPLC analysis of preparative HPLC fractions in the separation of menthyl carbamate diastereomers 1a and 1b. Fractions #1 and #2 show pure 1a. Fraction #3 shows a mixture of 1a and 1b. Fractions #4 and #5 show pure 1b.

Diastereomer 1a was purified to 99% isomeric purity by preparative reverse phase HPLC by loading 600–800 mg of 1a purified to 75% purity by the flash process, dissolved in 500 ml of 100 mM TEAA on to a Metachem ODS3 $8\mu$ column (Waters Prep LC 2000 System) and eluting under a gradient of 0 to 10% $CH_3CN$ in 100 mM TEAA over 16 min., 10 to 35% CH3CN over 80 min., then hold at 35% $CH_3CN$ for 32 min., at a flow rate of 40 ml/min., with UV detection at 260 nm. Fractions were collected and analyzed by the analytical reverse phase HPLC conditions above (FIG. 1b). Fractions with isomeric purity of at least 99% were combined, acidified to pH 2 with 6N HCl and extracted with ethyl acetate. The ethyl acetate fraction was washed with saturated NaCl, dried over anhydrous $Na_2SO_4$, concentrated under vacuum, precipitated with hexane, filtered, and dried to yield 300 to 500 mg of 1a as a bright yellow solid. $^1$H NMR (Acetone-d6) δ9.85, 2H, br; 9.10, 1H, br; 8.35, 1H, d; 8.15, 1H, d; 7.83, 1H, s; 7.43, 1H, br; 6.95, 1H, s; 6.70, 4H, m; 4.60, 3H, m; 1.90, 2H, m; 1.65, 2H, m; 1.45, 1H, m; 1.30, 2H, m; 0.89, 3H, d; 0.82, 3H, d; 0.78, 3H, d. Electrospray Mass Spectroscopy: 610 (M+Na), 588.5 (M+H), Diastereomer 1b is purified by the same preparative reverse phase HPLC process.

Example 3
Synthesis of Atropisomer Amine 2a

Diastereomer 1a (1.1 gm, 1.87 mmoles, 587.6 MW) was dissolved in 100 ml water and cooled to 0° C. Concentrated sulfuric acid (15 ml) was added dropwise to give a brownish solution (FIG. 2a). The temperature was allowed to rise to room temperature and the mixture was stirred overnight. The mixture was added slowly to 1.5 ml of ice water and then adsorbed on pre-equilibrated C-18 silica gel (4 cm length×3 cm diameter). The support was washed with water until the pH of the eluent was neutral. The crude product was eluted with 200 ml $CH_3OH$ which was concentrated under vacuum and dried to yield atropisomer 2a C-1 aminomethyl, C-19 carboxy fluorescein sulfate salt as an orange solid (0.93 gm, 95% yield, 503.4 MW). $^1$H NMR (methanol-d4) δ8.43, 1H, d; 8.34, 1H, d; 7.92, 1H, s; 7.23, 3H, m; 7.06, 1H, d; 6.98, 1H, d; 4.58, 2H, s.

The enantiomeric purity of hydrolyzed and purified 2a was analyzed by chiral column HPLC (Regies (S,S) Whelk-01 10-100 Kromasil FEC column, 25 cm length×4.6 mm ID). The sample 2a was dissolved in water and eluted with a gradient of 0 to 35% ethanol in water containing 0.1% acetic acid over 30 minutes at 1 ml/min. with 254 nm UV detection (FIG. 2c) and distinguished from the racemic mixture (FIG. 2b).

Example 4
Synthesis of Atropisomer Amine 2b

Diastereomer 1b is hydrolyzed, purified, and analyzed to give atropisomer 2b by the same processes as Example 3 (FIG. 2a).

Example 5
Synthesis of Atropisomeric Trifluoroacetamide 3a

Atropisomer 2a as the sulfate salt (0.93 gm, 1.84 mmoles, 503.4 MW) was dissolved in 15 ml ethanol. Triethylamine (1.8 ml, 13 mmoles) and ethyl trifluoroacetate (2.2 ml, 18 mmoles) were slowly added (FIG. 2a). The mixture was stirred at room temperature under argon for 2.5 hours. Volatiles were removed under vacuum and the resulting residue was dissolved in 300 ml ethyl acetate and washed with 2×50 ml of 5% HCl. The ethyl acetate fraction was dried over anhydrous $Na_2SO_4$, filtered and concentrated under vacuum to yield atropisomeric trifluoroacetamide 3a as an orange solid (0.92 gm, 100% yield, 501.4 MW). $^1$H NMR (methanol-d4) δ8.35, 1H, d; 8.15, 1H, d; 7.80, 1H, s; 6.82, 1H, s; 6.65, 4H, m; 4.82, 2H, s.

Example 6
Synthesis of Atropisomeric Trifluoroacetamide 3b

Atropisomer 2b is converted to atropisomeric trifluoroacetamide 3b by the same process and analyzed by the same methods as Example 5 (FIG. 2a).

Example 7
Synthesis of Atropisomeric NHS Ester 4a

Atropisomeric trifluoroacetamide 3a (0.92 gm, 1.83 mmoles, 501.4), N-hydroxysuccinimide (0.85 gm, 7.3 mmoles), and 1-[3-(dimethylamino)propyl]-3-ethylcarbodiimide hydrochloride (DAE) (1.05 gm, 5.5 mmoles) were dissolved in 24 ml ethyl acetate and 12 ml of 1-methyl-2-pyrrolidinone (NMP) and stirred at room temperature under argon for 2.5 hours (FIG. 3). The mixture was diluted with 300 ml ethyl acetate and washed with 2×80 ml of 5% HCl, dried over anhydrous $Na_2SO_4$, filtered, concentrated under vacuum, and adsorbed on silica gel. The silica gel with adsorbed product was loaded on the top of a dry-packed column of silica gel (12 cm length×3 cm ID) and eluted with ethyl acetate:hexane/2:1. Fractions containing atropisomeric NHS ester 4a were collected and combined, concentrated under vacuum and precipitated from hexane to yield 4a as a bright yellow solid (0.74 gm, 67% yield, 598.4 MW). $^1$H NMR (methanol-d4) δ8.42, 1H, d; 8.22, 1H, d; 7.95, 1H, s; 6.81, 1H, s; 6.68, 4H, m; 4.82, 2H, s; 2.85, 4H, s.

Example 8
Synthesis of Atropisomeric NHS Ester 4b

Atropisomeric trifluoroacetamide 3b is converted to atropisomeric NHS ester 4b by the same process and analyzed by the same methods as Example 7 (FIG. 3).

Example 9
Synthesis of 2-[(2-Fmoc-aminoethoxy)(hydroxyphosphoryl)oxy]acetic Acid NHS 5

Protected phosphodiester linker synthon 5 was prepared by reacting methyl glycolate 6 (4.5 eq.) with cyclic phosphoramidite Amino-Link™ 7 (1 eq.) (Connell (1987) *Bio-Techniques* 5:342–348; U.S. Pat. No. 4,757,151) and 4-N,N-dimethylaminopyridine (DMAP) (0.1 eq.). The mixture was stirred at ambient temperature for 1 hour. After the reaction was complete (TLC analysis), the solution was cooled with ice-bath and then treated with a solution of 3-chloroperoxybenzoic acid (4 eq.) in methylene chloride. The ice-bath was removed. After 30 minutes, an aqueous solution of $NaHSO_3$ (10%) was added. The mixture was diluted with ethyl acetate. The organic layer was washed with $NaHSO_3$ (10%), saturated solution of $NaHCO_3$, and dried with $Na_2SO_4$. The crude product was purified by flash chromatography to afford ester 8, which was heated at reflux for 3 hours (36 mM, 1 eq.) in methylethylketone and NaI (10 eq.). The crude demethylated phosphodiester was dissolved in 0.3 M solution of LiOH (5 eq.) in $H_2O/CH_3OH$:1/3) and stirred overnight to cleave the methyl ester. Solvent was removed to afford crude compound 9 which was then dissolved in aqueous $Na_2CO_3$ (5%). N-(9-Fluorenyhnethoxy-carbonyloxy)succinimide (FmocOSu, 1.5 eq.) in THF was added in one portion and stirred at ambient temperature for 3 hours. The crude product was diluted with ethyl acetate and washed with 10% aqueous HCl. The organic layer was dried with $Na_2SO_4$, filtered, concentrated under vacuum, and purified by flash chromatography to afford Fmoc-acid 10 as a yellow oil.

Fmoc-acid 10 was dissolved in anhydrous $CH_2Cl_2$ (1 eq.). N-hydroxysuccinimide (4 eq.) was added. The solution was cooled with an ice-bath and then treated with dicyclohexyl carbodiimide (DCC, 2 eq.). The ice-bath was then removed, and stirring was continued for 2 hours (with TLC analysis). When the reaction was complete, ethyl acetate was added and the solution was washed with 5% aqueous HCl. Removal of solvent gave 2-[(2-Fmoc-aminoethoxy)(hydroxyphosphoryl)oxy]acetic acid NHS 5 (FIG. 4).

Example 10
Synthesis of 7-propargylphosphorylamino-7-deaza-ddATP 11

7-Deaza-7-propargylamino-ddATP 12 (7-(3-amino-1-propynyl)-2',3'-dideoxy-7-deazaadenosine-5'-triphosphate; U.S. Pat. Nos. 5,047,519 and 5,151,507) was suspended in 250 mM bicarbonate (pH 9.0) and a solution of 2-[(2-Fmoc-aminoethoxy)(hydroxyphosphoryl)oxy]acetic acid NHS 5 in DMSO was added. After 1 hour, the reaction mixture was purified by HPLC (AX-300 anion exchange). The product fractions were collected, concentrated to dryness, and purified by RP HPLC (C-18 reverse phase) to afford Fmoc-linker ddATP 13. Concentrated ammonium hydroxide (28–30%) was added to Fmoc-linker ddATP 13 and the solution was heated to 55° C. for 20 minutes. Concentration under vacuum gave crude 7-propargylphosphorylamino-7-deaza-ddATP 11 which was purified by C-18 reverse phase HPLC (FIG. 5).

Example 11
Synthesis of Fmoc-aminomethyl-NHS-FAM 14

Fmoc-aminomethyl-NHS-FAM 14 was prepared by reacting the fluorenylmethoxy-carbonyloxy ester of N-hydroxysuccinimide (Fmoc-OSu) with the HCl salt of p-aminomethylbenzoic acid (both commercially available) in the presence of base to form the expected N-Fmoc derivative. This product was then reacted with N-hydroxysuccinimide in the presence of DCC to form the NHS ester of the benzoic acid carboxyl group. This NHS-ester, N-Fmoc derivative of p-aminomethylbenzoic acid having the structure:

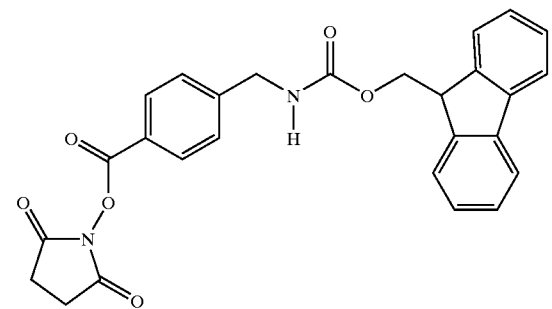

was then reacted with atropisomer C-1 aminomethyl, C-19 carboxy fluorescein 2a, purified by the method of Example 2, followed by reaction with N-hydroxysuccinimide in the presence of DCC to produce substantially pure atropisomer, Fmoc-aminomethyl-NHS-FAM 14 (FIG. 6).

Example 12
Synthesis of Aminomethylbenzamide-aminomethyl-FAM-propargylphosphorylamino-ddATP 15

A solution of Fmoc-aminomethyl-NHS-FAM 14 in DMSO was added to 7-propargylphosphorylamino-7-deaza-ddATP 11 suspended in 250 mM bicarbonate (pH 9.0). The reaction mixture was placed in the dark at ambient temperature for 2 hours. The Fmoc-amino protected product 16 was purified by HPLC (AX-300 anion exchange), then heated at 55° C. in concentrated ammonium hydroxide (28–30%) for 20 minutes to hydrolyze the Fmoc group. Concentration under vacuum gave crude, substantially pure atropisomer, aminomethylbenzamide-aminomethyl-FAM-propargylphosphorylamino-ddATP 15 which was purified by C-18 reverse phase HPLC (FIG. 6).

Example 13
Synthesis of NHS-rhodamine Dye 17

Bicyclic amine 18 (12.8 gm, 47 mmole, U.S. Pat. No. 5,688,808), 1-bromo-3-chloropropane (29.3 gm, 187 mmole), sodium iodide (56.4 gm, 376 mmole) and sodium bicarbonate (7.9 gm, 94 mmole) was refluxed in 150 ml $CH_3CN$ for 18 hours. The mixture was cooled to room temperature, filtered, and evaporated. The filter cake was washed with 300 ml hexane which was combined with the filtrate and washed with 2×50 ml water and 50 ml saturated NaCl, dried over $MgSO_4$, filtered, and concentrated under vacuum. The product was purified by chromatography on silica gel, eluting with hexane/ethyl acetate:20/1, to give tricyclic amine pivalate ester 19 as a pale yellow oil (9.5 gm, 30 mmole, 64% yield). The ester of 19 was hydrolyzed in a solution of lithium hydroxide monohydrate (2.6 gm, 60 mmole) in 15 ml water and 120 ml methanol. After stirring for one hour at room temperature, the mixture was concentrated under vacuum and dissolved in 30 ml 1M HCl which was extracted with 3×100 ml of diethylether. The combined ether extracts were washed with 50 ml of 200 mM pH 7 phosphate buffer, dried over $MgSO_4$, filtered and concentrated under vacuum to give tricyclic amine 20 as a brown solid (FIG. 7). Tricyclic amine 20 and 3,6-dichloro, 4-isopropylcarboxylate phthalic anhydride 21 were refluxed in toluene to give Friedel-Craft acylation product ketone 22 (Abs. max 400 nm) (FIG. 8).

Cyclization of 22 with 20 in phosphoryl trichloride and chloroform at reflux gave 23 as a mixture of isopropylcarboxylate regioisomers. After cleavage of the isopropyl group, the rhodamine carboxylic acid 24 was converted to NHS-rhodamine dye 17 (FIG. 8).

Example 14
Synthesis of Phosphate-linker, Energy-transfer Terminator ddATP 25

Aminomethylbenzamide-aminomethyl-FAM-propargylphosphorylamino-ddATP 15 from Example 12 was suspended in a solution of 250 mM bicarbonate (pH 9.0). A solution of NHS ester 17 (U.S. Pat. No. 5,847,162 for synthesis) in DMSO was added. The reaction mixture was placed in the dark at ambient temperature for 2 hours. Purification was done by HPLC, AX-300 anion exchange and then C-18 reverse phase to afford pure energy-transfer ddATP terminator 25 (FIG. 9).

Example 15
Synthesis of bis-trifluoroacetamide Rhodamine NHS 27

Rhodamine dye 28 was converted to the bis-trifluoroacetamide 29 by treatment with trifluoroacetic anhydride and triethylamine in diethylether at room temperature. The carboxylic acid was converted to the NHS ester with dicyclohexylcarbodiimide and N-hydroxysuccinimide to give bis-trifluoroacetamide rhodamine NHS 27 (FIG. 10).

Example 16
Synthesis of Aminomethylbenzamide-aminomethyl-FAM-propargylethoxyamino-ddTTP 32

5-(3-Aminoethoxy1-propynyl)-2',3'-dideoxythymidine-5'-triphosphate 30 (U.S. Pat. No. 5,821,356) was reacted with substantially pure atropisomer, Fmoc-aminomethyl-NHS-FAM 14 under the same conditions as Example 12 to give Fmoc-aminomethylbenzamide-aminomethyl-FAM-propargylethoxyamino-ddTTP 31 which was purified by anion-exchange HPLC. The Fmoc group of 31 was cleaved to give substantially pure atropisomer, aminomethylbenzamide-aminomethyl-FAM-propargylethoxyamino-ddTTP 32 (FIG. 11).

Example 17
Synthesis of Energy-transfer Terminator ddTTP 26

Following the conditions of Example 14, substantially pure atropisomer, aminomethylbenzamide-aminomethyl-FAM-propargylethoxyamino-ddTTP 32 was suspended in a solution of 250 mM bicarbonate (pH 9.0). A solution of bis-trifluoroacetamide rhodamine NHS ester 27 in DMSO was added. The reaction mixture was placed in the dark at ambient temperature for 2 hours. Ammonium hydroxide was added to cleave the trifluoroacetamide groups. Purification was done by HPLC, AX-300 anion exchange and then C-18 reverse phase to afford pure energy-transfer ddTTP terminator 26 (FIG. 12).

Example 18
Sequencing of pGEM with Phosphate-linker, Energy-transfer Terminator ddATP 25

Following the conditions of U.S. Pat. Nos. 5,770,716; 5,948,648; and 6,096,875, the energy-transfer ddATP terminator 25 was used with other standard reagents in a Sanger-type, one-color automated DNA sequencing experiment. The terminator nucleotide 25 was tested as the racemic mixture of atropisomers (top electropherogram) and as a substantially pure atropisomer (bottom electropherogram) shown in FIGS. 13a and 13b.

The dye-terminator sequencing reactions were performed using AmpliTaq DNA Polymerase, FS following protocols provided in the ABI PRISM™ Dye Terminator Cycle Sequencing Core Kit Manual (Applied Biosystems p/n 402116). Sequencing of the pGEM-3Zf(+) template was conducted with unlabelled -21 M13 sequencing primer (forward). Reagents, including buffer, unlabelled primer, AmpliTaq DNA Polymerase, FS, were from an ABI PRISM™ Dye Terminator Core Kit (Applied Biosystems p/n 402117). The dNTP mix consisted of 2 mM each of dATP, dCTP, dITP, and dUTP or dTTP. A premix of reaction components was prepared including: 5× Buffer 4.0 µL; dNTP mix 1.0 µL; Template:pGEM®-3Zf(+), 0.2 µg/µL, 2.0 µL; Primer: -21 M13 (forward), 0.8 pmol/µL, 4.0 µL; AmpliTaq DNA Polymerase, FS, 0.5 µL; and H$_2$O 3.5 µL, wherein all quantities are given on a per reaction basis.

Reactions were assembled in 0.5 ml tubes adapted for the Perkin-Elmer 480 DNA Thermal Cycler (Applied Biosystems p/n N801-100 or 0.2 ml tubes for the Applied Biosystems Gene Amp PCR System 9700). From 1 to 250 pmol of the dye terminator was added to each reaction. 30 µL of mineral oil was added to the top of each reaction to prevent evaporation (when using the Applied Biosystems 480 Thermal Cycler). Reaction volumes were 20 µL, including 15 µL of the above reaction premix, a variable amount of dye labelled terminator, and a sufficient volume of water to bring the total reaction volume up to 20 µL. Reactions were thermocycled as follows: 96° C. for 30 sec, 50° C. for 15 sec, and 60° C. for 4 min, for 25 cycles; followed by a 4° C. hold cycle.

All reactions were purified by spin-column purification on Centri-Sep spin columns according to manufacturer's instructions (Princeton Separations p/n CS-901). Gel material in the column was hydrated with 0.8 mL deionized water for at least 30 minutes at room temperature. After the column was hydrated and it was determined that no bubbles were trapped in the gel material, the upper and lower end caps of the column were removed, and the column was allowed to drain by gravity. The column was then inserted into the wash tubes provided in the kit and centrifuged in a variable speed microcentrifuge at 1300 g for 2 minutes, removed from the wash tube, and inserted into a sample collection tube. The reaction mixture was carefully removed from under the oil and loaded onto the gel material and the tube re-centrifuged. Eluted samples were then dried in a vacuum centrifuge.

Prior to loading onto a sequencing gel, the dried samples were resuspended in 25 µL of Template Suppression Reagent (Applied Biosystems p/n 401674), vortexed, heated to 95° C. for 2 minutes, cooled on ice, vortexed again, and centrifuged (13,000×g). 10 µL of the resuspended sample was aliquoted into sample vials (Applied Biosystems p/n 401957) adapted for the ABI PRISM™ 310 Genetic Analyzer (Applied Biosystems p/n 310-00-100/120). Electrophoresis on the 310 Genetic Analyzer was performed with sieving polymers and capillaries specially adapted for DNA sequencing analysis (PE Applied Biosystems p/n 402837 or 4313087 (polymer) and p/n 402840 (capillary)). In each case, the sieving polymer included nucleic acid denaturants. Samples were electrokinetically injected onto the capillary for 30 sec at 2.5 kV, and run for up to 2 hr at 10 to 12.2 kV with the outside wall of the capillary maintained at 50° C. to generate electropherograms as sequencing data (FIGS. 13a–d).

Figure 13A:
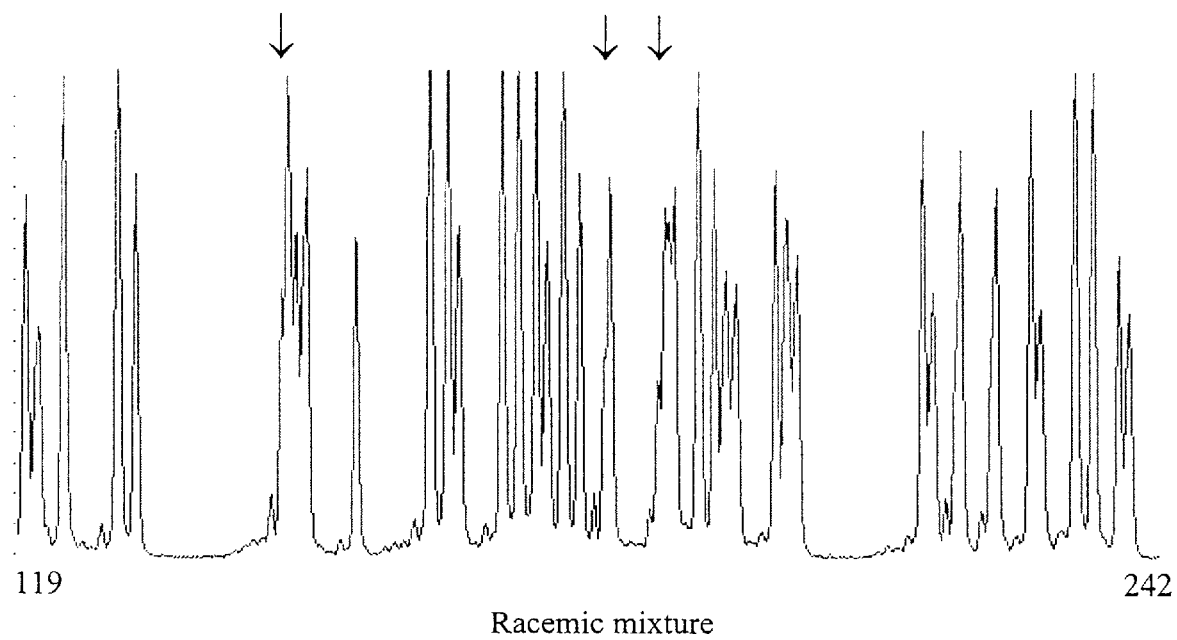
FIG. 13a shows DNA sequencing of pGEM with phosphate-linker, energy-transfer terminator ddATP 25, fragment size 119–242 bp.
Figure 13A:
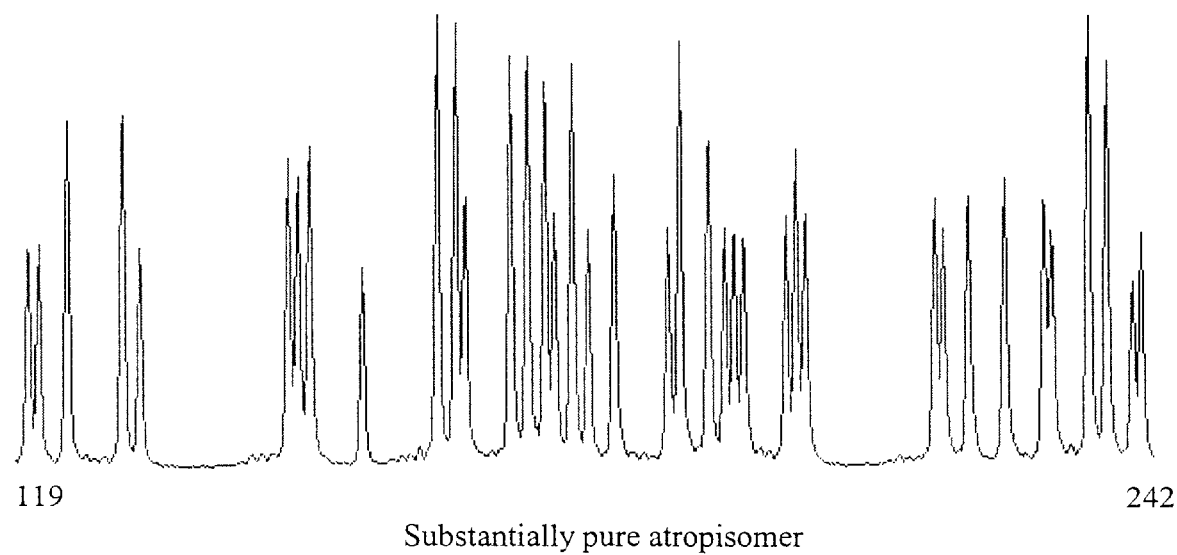
Figure 13B:
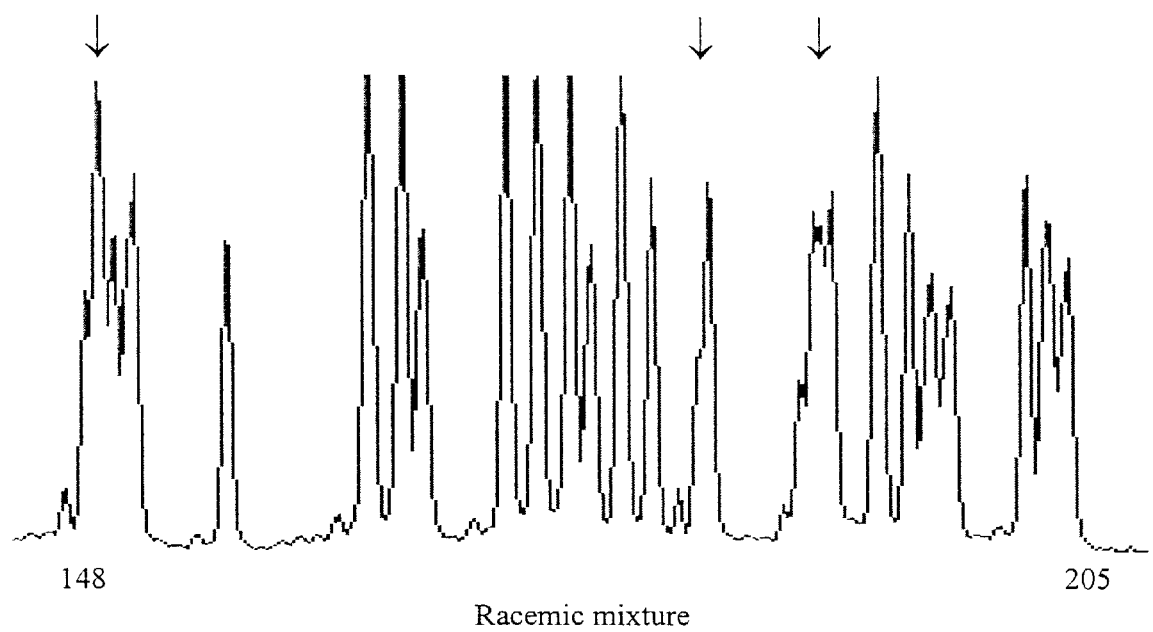
FIG. 13b shows DNA sequencing of pGEM with phosphate-linker, energy-transfer terminator ddATP 25, fragment size 148–205 bp.
Figure 13B:
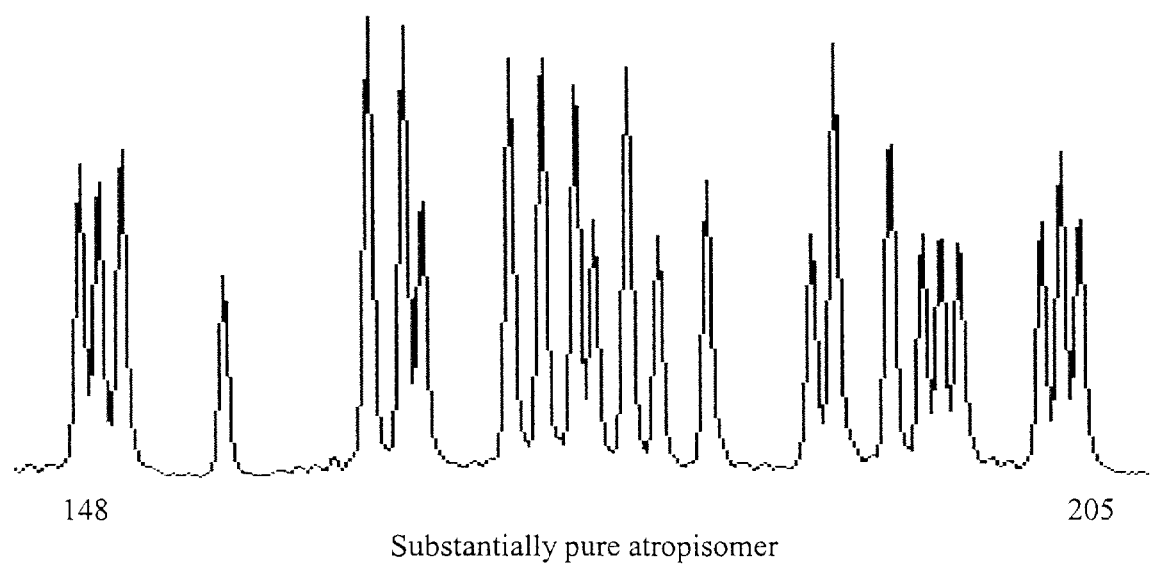

The electropherograms in FIGS. 13a and 13b show the specific incorporation of the energy-transfer terminator 25 onto the 3' terminus of primer extension, polynucleotide fragments during single color sequencing reactions. The electropherograms plot the fluorescence intensity emitted (Emission maxima about 650 nm) by the acceptor rhodamine dye of the labelled fragments between about 20 to about 600 nucleotides in length as a function of time during an electrophoresis run on the ABI PRISM™ 310 Genetic Analyzer.

Eluting fragments from 119 to 242 base pairs are plotted in FIG. 13a. Each of the fragments was 3' terminated by energy-transfer terminator 25. FIG. 13b shows a more magnified view of fragments 148 to 205 base pairs. The three regions under the arrows in FIGS. 13a and 13b illustrate the surprising and unexpected improvement in separating fragments labelled with the substantially pure atropisomer form of 25 (bottom panels) relative to the separation of fragments labelled with the racemic mixture of 25. Better resolution of the fragments was observed in the bottom electropherogram with the substantially pure atropisomer than with the racemic mixture of atropisomers in 25. The locations marked with arrows are particular loci where substantially pure atropisomer form of 25 provided the unexpected benefit of better resolution. By contrast, use of the racemic mixture of atropisomeric form of 25 in labelling the chiral primer extension products led to diastereomeric populations of fragments which migrate electrophoretically at different rates, as exemplified by the broad, overlapping, and split peaks under the arrows in the top electropherogram.

Additionally, the bottom electropherogram shows more even peak heights throughout the sequencing ladder than was observed in the top electropherogram with the racemic mixture of atropisomers in 25.

Example 19
Sequencing of pGEM with Sulfonate-linker, Energy-transfer Terminator ddATP 33

Figure 13C:
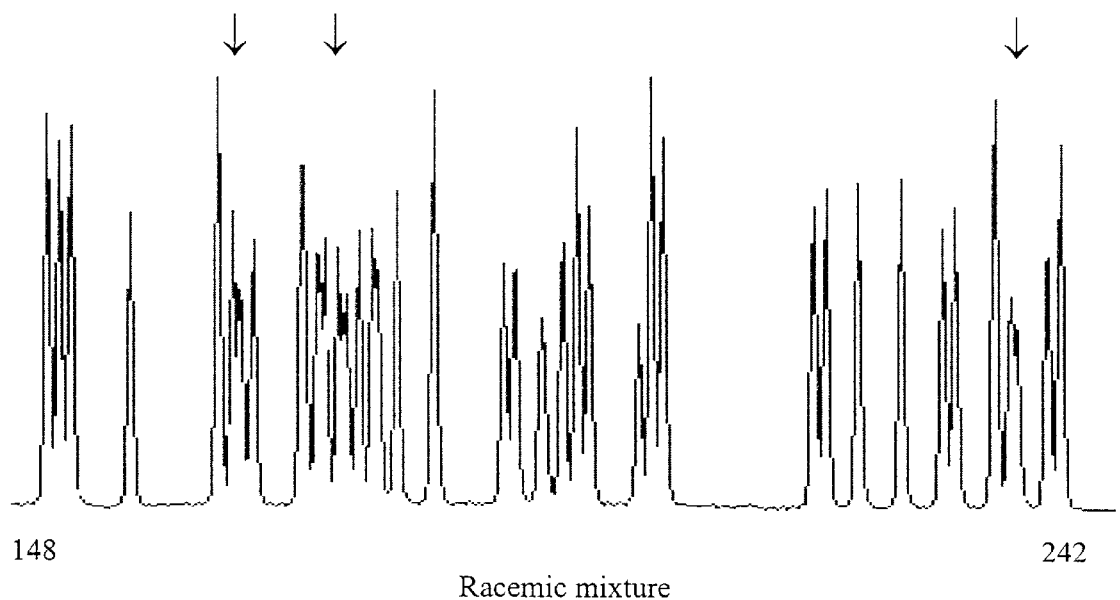
FIG. 13c shows DNA sequencing of pGEM with sulfonate-linker, energy-transfer terminator ddATP 33, fragment size 148–242 bp.
Figure 13C:
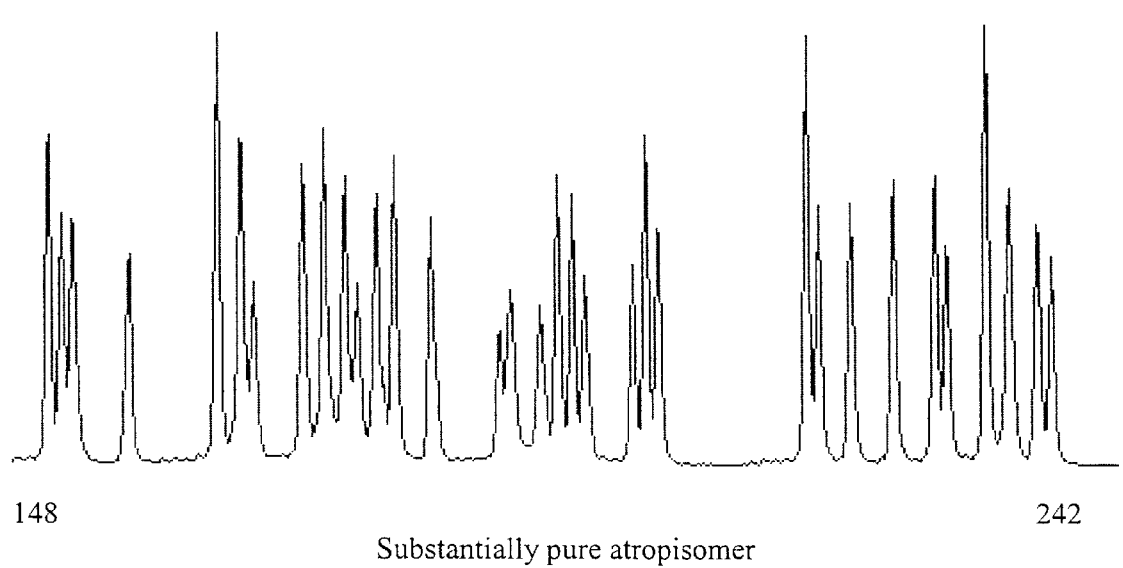
Figure 14:
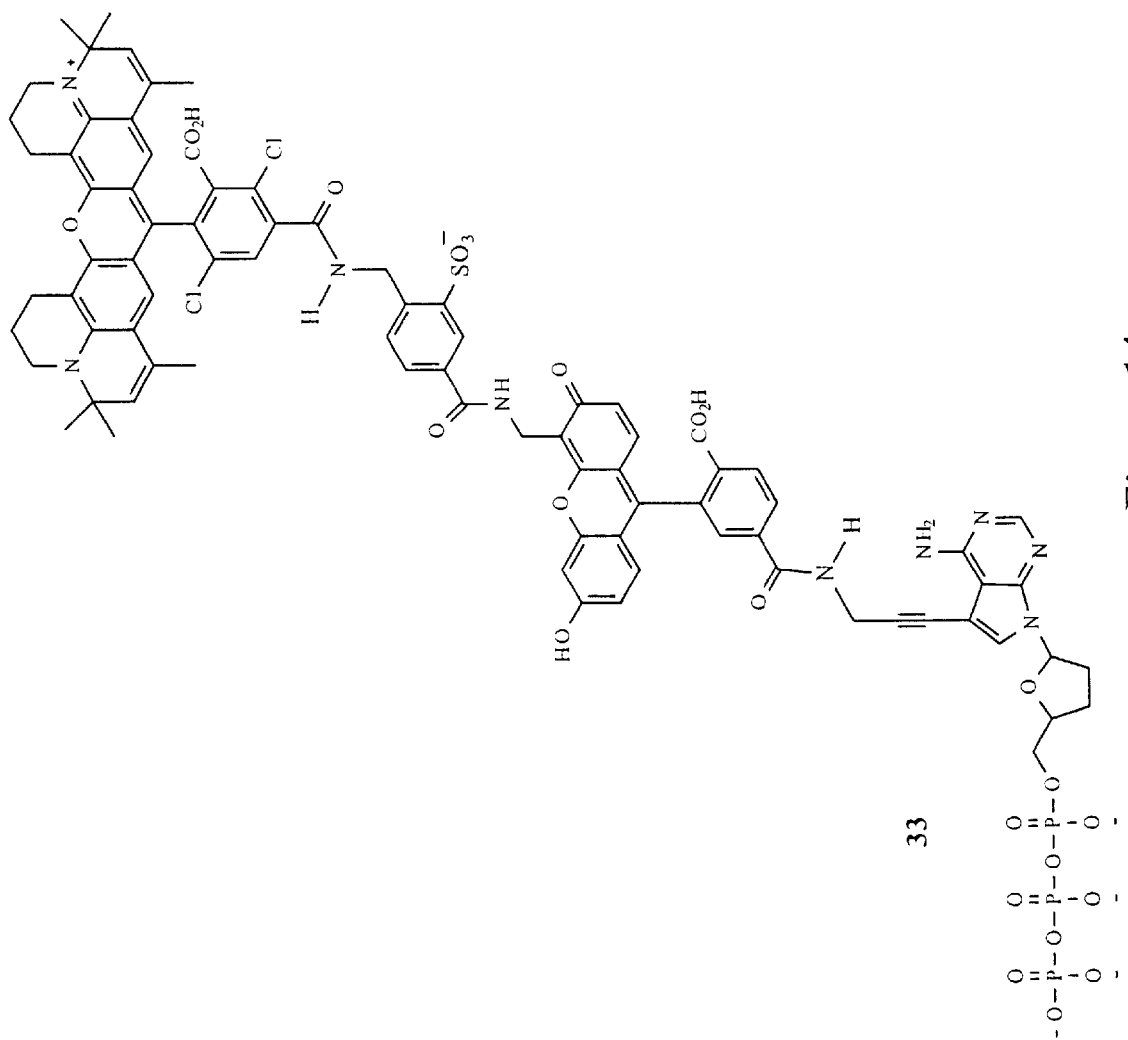
FIG. 14 shows the structure of sulfonate-linker, energy-transfer terminator ddATP 33.

Following the general synthesis routes and conditions of the previous Examples, substantially pure atropisomer, sulfonate-linker, energy-transfer terminator ddATP 33 (FIG. 14) was synthesized. Following the protocol and conditions of Example 18, 33 was used in single-color sequencing the pGEM target. Separately, the racemic mixture of 33 was also used in the same single-color sequencing experiment. Eluting fragments from 148 to 242 base pairs are plotted in FIG. 13c. Each of the fragments was 3' terminated by energy-transfer terminator 33. The three regions under the arrows in FIG. 13c illustrate the surprising and unexpected improvement in separating fragments labelled with the substantially pure atropisomer form of 33 (bottom panel) relative to the separation of fragments labelled with the racemic mixture of 33 (top panel). Better resolution of the fragments was observed in the bottom electropherogram with the substantially pure atropisomer than with the racemic mixture of atropisomers in 33.

Example 20
Sequencing of pGEM with Energy-transfer Terminator ddGTP 34

Figure 13D:
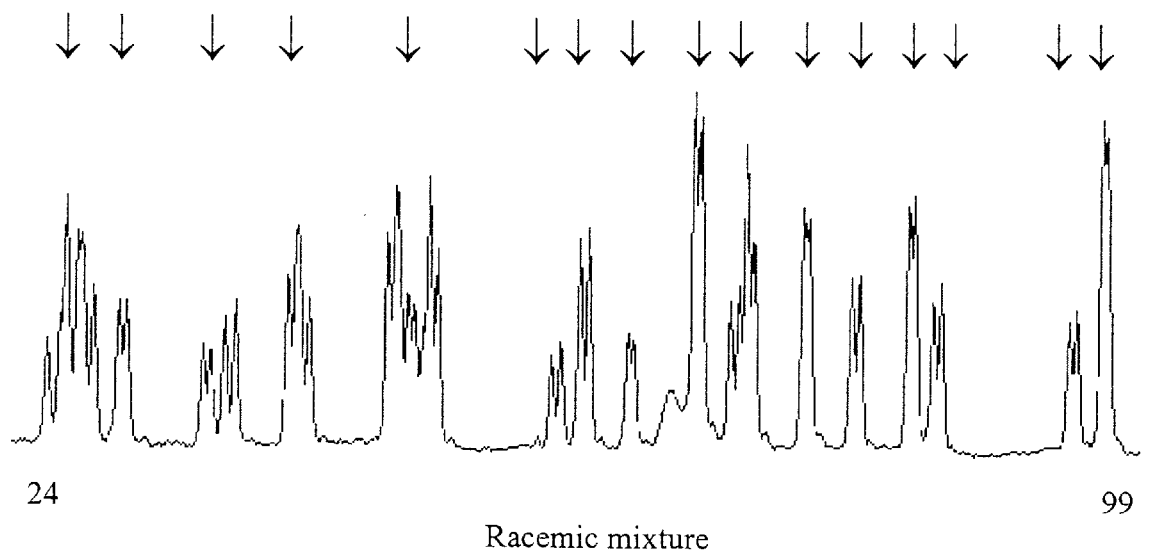
FIG. 13d shows DNA sequencing of pGEM with energy-transfer terminator ddGTP 34, fragment size 24–99 bp.
Figure 13D:
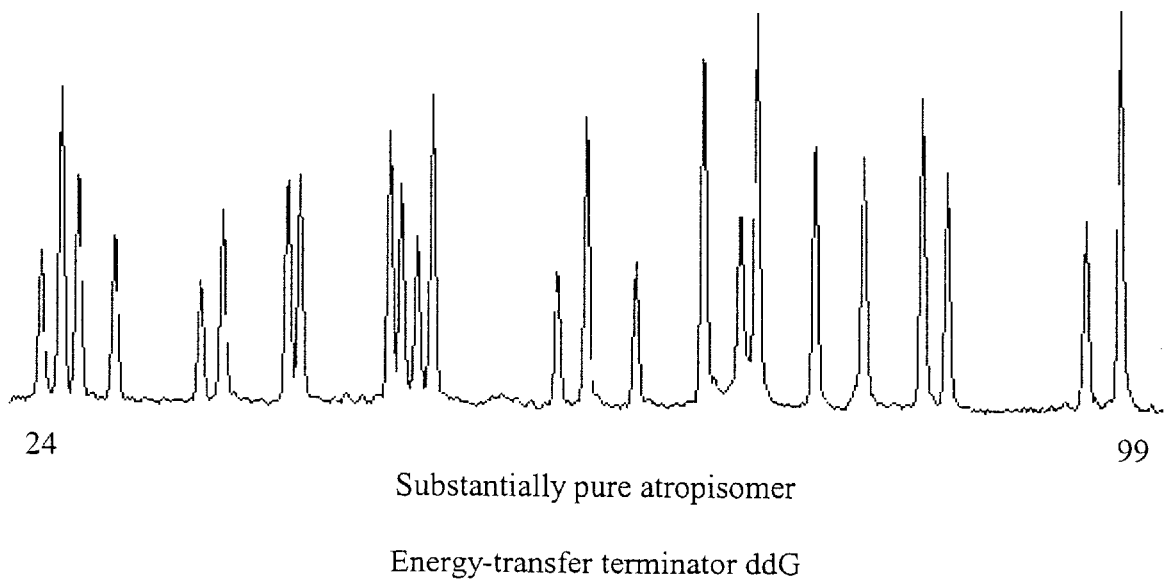
Figure 15:
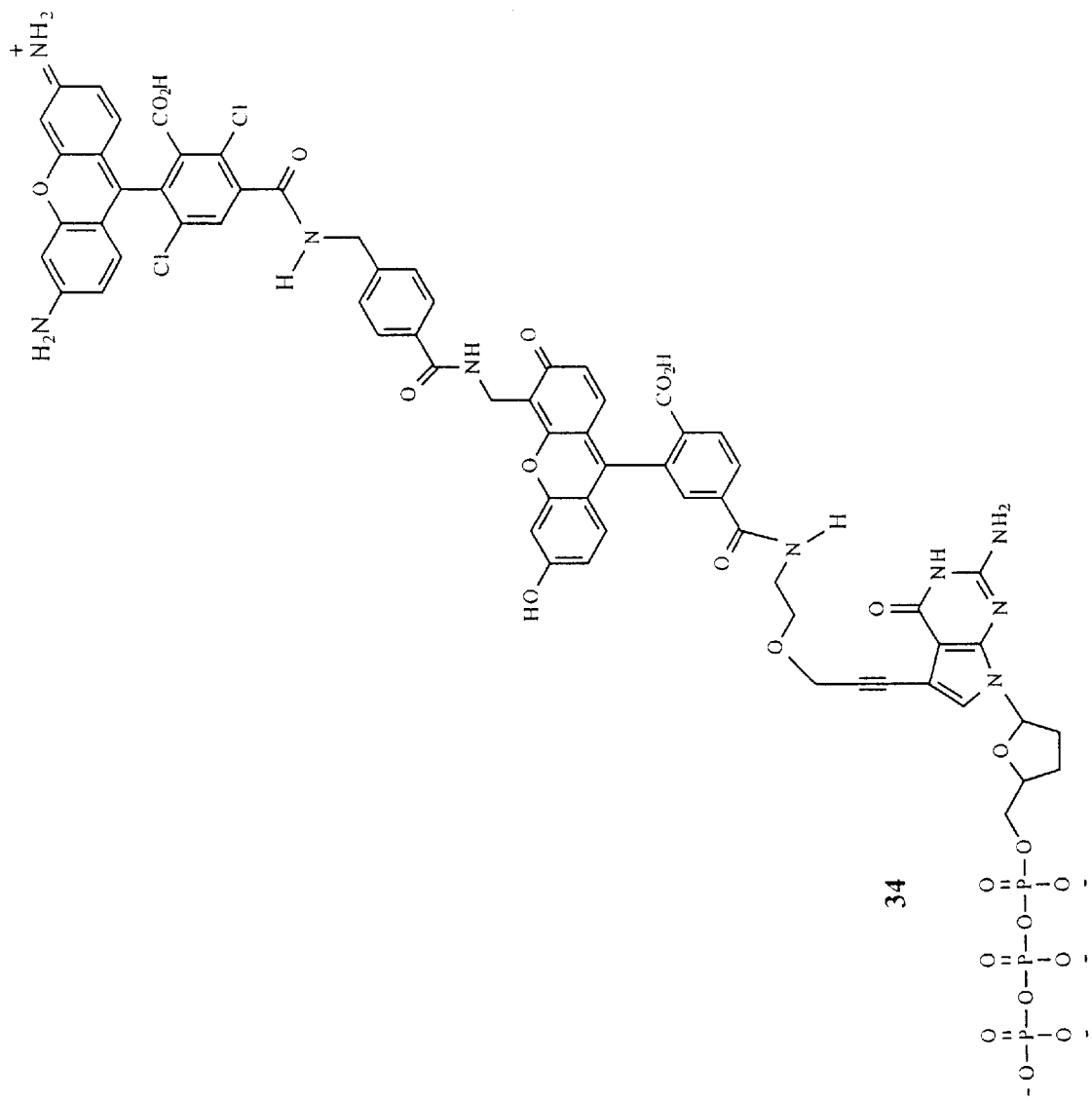
FIG. 15 shows the structure of energy-transfer terminator ddGTP 34.

Following the general synthesis routes and reaction conditions of the previous Examples, energy-transfer terminator ddGTP 34 (FIG. 15) was synthesized. The atropisomer forms were separated at the final stage of synthesis, i.e. compound 34, by reverse-phase HPLC. Following the protocol and conditions of Example 18, a substantially pure atropisomer of 34 was used in single-color sequencing the pGEM target. Separately, the racemic mixture of 34 was also used in the same single-color sequencing experiment. Eluting fragments from 24 to 99 base pairs, detected at about 535 nm, are plotted in FIG. 13d. Each of the fragments was 3' terminated by energy-transfer terminator 34. The regions under the arrows in FIG. 13d illustrates the surprising and unexpected improvement in separating fragments labelled with the substantially pure atropisomer form of 34 (bottom panel) relative to the separation of fragments labelled with the racemic mixture of 34 (top panel). Better resolution of virtually every fragment was observed in the bottom electropherogram with the substantially pure atropisomer than with the racemic mixture of atropisomers in 34. The locations marked with arrows are particular loci where substantially pure atropisomer form of 34 provided the unexpected benefit of better resolution. Every fragment in the bottom panel, labelled with racemic 34, separates into two peaks, detracting from the utility of the data.

All publications cited herein are incorporated by reference, and to the same extent as if each individual publication was specifically and individually indicated to be incorporated by reference.

Although only a few embodiments have been described in detail above, those having ordinary skill in the chemical and molecular biology arts will clearly understand that many modifications are possible in the illustrated embodiments without departing from the teachings thereof. All such modifications are intended to be encompassed within the following claims.

We claim:

1. A compound having the structure:

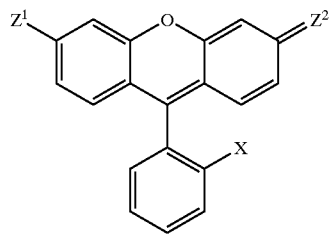

$Z^1$ is OH, $NH_2$, NHR, or $NR_2$, wherein each R is independently hydrogen, $C_1$–$C_{12}$ alkyl, phenyl, benzyl, aryl, heterocycle, or a linking moiety;

$Z^2$ is O, $NH_2$, $^+$NHR, $^+NR^2$, wherein each R is independently hydrogen, $C_1$–$C_{12}$ alkyl, phenyl, benzyl, aryl, heterocycle, or a linking moiety;

X is carboxylate or sulfonate;

and said structure includes aryl-substituted forms thereof; wherein the compound is atropisomerically enriched.

2. The substantially pure atropisomer compound of claim 1 wherein $Z^1$ is OH, $Z^2$ is O, and X is carboxylate.

3. The compound of claim 1 wherein $Z^1$ is $NR_2$, $Z^2$ is $^+NR_2$, and X is carboxylate.

4. The compound of claim 1 having the structure:

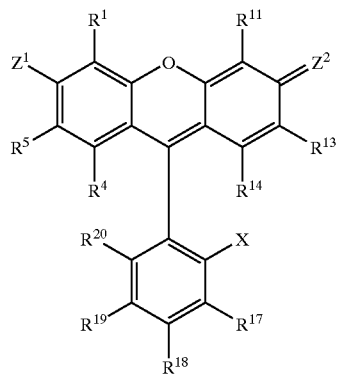

wherein at least one of $R^1$, $R^4$, $R^5$, $R^{11}$, $R^{13}$ $R^{14}$, $R^{17}$, $R^{18}$, $R^{19}$, $R^{20}$, $Z^1$, or $Z^2$ is a linking moiety selected from the group consisting of azido, monosubstituted primary amine, disubstituted secondary amine, thiol, hydroxyl, halide, epoxide, N-hydroxysuccinimidyl ester, carboxyl, isothiocyanate, sulfonyl chloride, sulfonate ester, silyl halide, chlorotriazinyl, succinimidyl ester, pentafluorophenyl ester, maleimide, haloacetyl, epoxide, alkylhalide, allyl halide, aldehyde, ketone, acylazide, anhydride, iodoacetamide and an activated ester.

5. The compound of claim 4 wherein one of $R^1$ and $R^{11}$ is a linking moiety.

6. The compound of claim 4 comprising one or more substituents $R^1$, $R^4$, $R^5$, $R^{11}$, $R^{13}$, $R^{14}$, $R^{17}$, $R^{18}$, $R^{19}$, and $R^{20}$, each of which is independently flourine, chlorine, $C_1$–$C_8$ alkyl, carboxylate, sulfate, sulfonate, alkylsulfonate, aminomethyl (—$CH_2NH_2$), aminoalkyl, 4-dialkylaminopyridinium, hydroxymethyl (—$CH_2OH$), methoxy (—$OCH_3$), hydroxyalkyl (—ROH), thiomethyl (—$CH_2SH$), thioalkyl (—RSH), alkylsulfone (—$SO_2R$), arylthio (—SAr), arylsulfone (—$SO_2Ar$), sulfonamide (—$SO_2NR_2$), alkylsulfoxide (—SOR), arylsulfoxide (—SOAr), amino (—$NH_2$), ammonium (—$NH_3^+$), amido (—$CONR_2$), nitrile (—CN), $C_1$–$C_8$ alkoxy (—OR), phenoxy, phenolic, tolyl, phenyl, aryl, benzyl, heterocycle, phosphonate, phosphate, quaternary amine, sulfate, polyethyleneoxy, and linking moiety.

7. The compound of claim 4 wherein $R^4$ and $R^5$ taken together form benzo.

8. The compound of claim 4 wherein at least one of $R^1$, $R^4$, $R^5$, $R^{11}$, $R^{13}$, and $R^{14}$ is an electron-deficient heterocycle selected from 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, pthalazine, quinazoline, quinoxaline, 3-(1,2,4-N)-triazolyl, 5-(1,2,4-N)-triazolyl, 5-tetrazolyl, 4-(1-O, 3-N)-oxazole, 5-(1-O, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, and benzimidazole.

9. The compound of claim 4 wherein at least one of $R^1$, $R^4$, $R^5$, $R^{11}$, $R^{13}$, and $R^{14}$ is phenyl or substituted phenyl.

10. The compound of claim 4 wherein at least one of $R^1$, $R^4$, $R^5$, $R^{11}$, $R^{13}$, and $R^{14}$ is naphthyl or substituted naphthyl.

11. The compound of claim 4 wherein at least one of $R^1$, $R^4$, $R^5$, $R^{11}$, $R^{13}$, and $R^{14}$ is fluorine or chlorine.

12. The compound of claim 4 wherein at least one of $R^1$, $R^4$, $R^5$, $R^{11}$, $R^{13}$, and $R^{14}$ is 2-pyridyl or 3-pyridyl.

13. The compound of claim 4 wherein at least one of $R^1$, $R^4$, $R^5$, $R^{11}$, $R^{13}$, and $R^{14}$ is 2-quinolyl or 3-quinolyl.

14. The compound of claim 4 wherein at least one of $R^1$, $R^4$, $R^5$, $R^{11}$, $R^{13}$, and $R^{14}$ is methoxy (—$OCH_3$).

15. The compound of claim 4 wherein at least one of $R^1$, $R^4$, $R^5$, $R^{11}$, $R^{13}$, and $R^{14}$ is aminomethyl (—$CH_2NH_2$).

16. The compound of claim 4 wherein at least one of $R^{17}$, $R^{18}$, $R^{19}$, and $R^{20}$ is chlorine.

17. The compound of claim 4 wherein at least one of $R^{17}$, $R^{18}$, $R^{19}$, and $R^{20}$ is fluorine.

18. The compound of claim 4 wherein at least one of $R^{17}$, $R^{18}$, $R^{19}$, and $R^{20}$ is 4-dialkylaminopyridinium.

19. The compound of claim 4 wherein at least one of $R^{17}$, $R^{18}$, $R^{19}$, and $R^{20}$ is thiophenyl.

20. The compound of claim 4 wherein at least one of $R^{17}$, $R^{18}$, $R^{19}$, and $R^{20}$ is thio-4-carboxyphenyl.

21. The compound of claim 4 wherein at least one of $R^{18}$ and $R^{19}$ is carboxyl and the other is hydrogen.

22. The compound of claim 4 wherein one of $R^{18}$ and $R^{19}$ is a linking moiety and the other is hydrogen.

23. The compound of claim 4 wherein $R^{17}$ and $R^{20}$ are chlorine; one $R^{18}$ and $R^{19}$ is a linking moiety and the other is hydrogen; and X is carboxyl.

24. The compound of claim 4 comprising a first bridging group which when taken together with a $Z^1$ nitrogen, the $Z^1$-bonded carbon, and the $R^1$-bonded carbon, forms a first ring structure having from 4 to 7 members; and optionally, a second bridging group which when taken together with a $Z^2$ nitrogen, the $Z^2$-bonded carbon, and the $R^{11}$-bonded carbon forms a second ring structure having from 4 to 7 members.

25. The compound of claim 24 wherein one or both of the first and second ring structures has five members.

26. The compound of claim 25 wherein the five membered ring structure includes one gem disubstituted carbon.

27. The compound of claim 26 wherein the gem substituents are $C_1$–$C_8$ alkyl.

28. The compound of claim 27 wherein the gem substituents are methyl.

29. The compound of claim 25 wherein the five membered ring is substituted with a linking moiety.

30. A compound selected from the group consisting of the structures.

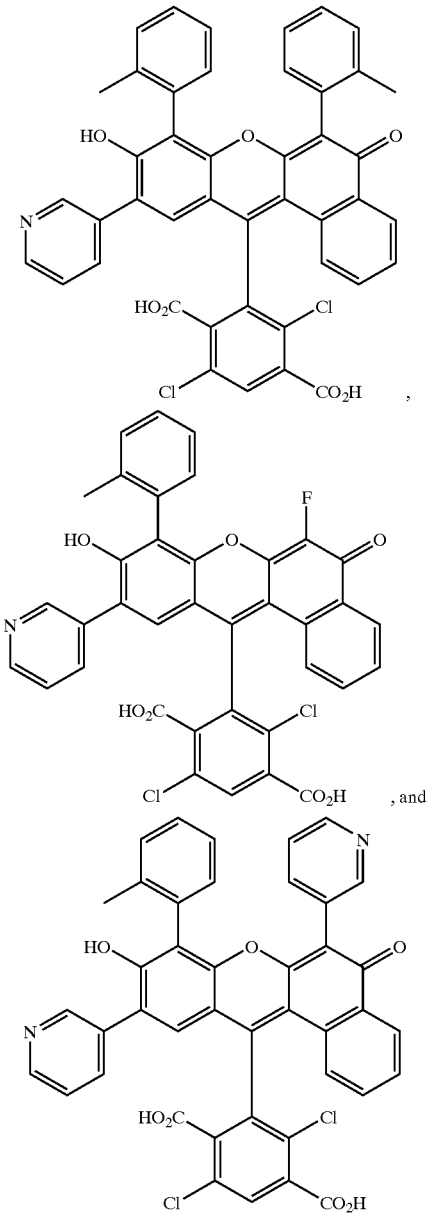

wherein the compound atropisomerically enriched.

31. The compound of claim 1 wherein the compound is a substantially pure atropisomer.

32. A labelled nucleoside or nucleotide having the formula:

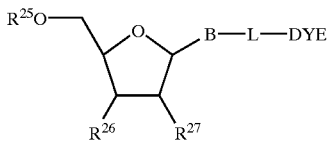

wherein DYE is a substantially pure atropisomer of a xanthene compound having the structure:

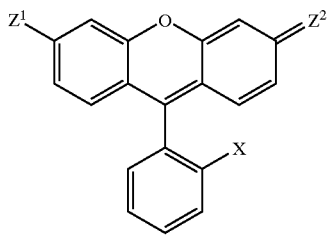

$Z^1$ is OH, $NH_2$, NHR, or $NR_2$, wherein each R is independently hydrogen, $C_1$–$C_{12}$ alkyl, phenyl, benzyl, aryl, heterocycle, or a linking moiety;

$Z^2$ is O, $^+NH_2$, $^+NHR$, or $^+NR_2$, wherein each R is independently hydrogen, $C_1$–$C_{12}$ alkyl, phenyl, benzyl, aryl, heterocycle, or a linking moiety;

X is carboxylate or sulfonate;

B is a nucleobase;

L is a linker;

$R^{25}$ is H, monophosphate, diphosphate, triphosphate, thiophosphate, or phosphate analog;

$R^{25}$ and $R^{27}$, when taken alone, are each independently H, HO, F or other moiety which blocks polymerase-mediated target-directed polymerization, or when taken together $R^{26}$ and $R^{27}$ form 2'-3'-didehydroribose; and wherein DYE is optionally aryl-substituted.

33. The labelled nucleoside or nucleotide of claim 32 wherein B is selected from the group consisting of uracil, thymine, cytosine, adenine, 7-deazaadenine, guanine, and 7-deazaguanosine.

34. The labelled nucleoside or nucleotide of claim 32 in which L is:

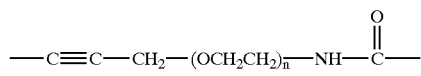

wherein n is 0, 1, or 2.

35. The labelled nucleoside or nucleotide of claim 32 which is enzymatically incorporatable.

36. The labelled nucleoside or nucleotide of claim 32 which is a terminator.

37. The labelled nucleoside or nucleotide of claim 33 which has the structure:

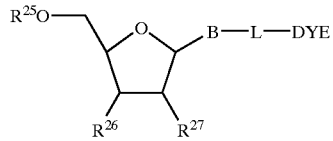

wherein $R^{26}$ and $R^{27}$, when taken alone, are each independently H, F or other moiety which blocks polymerase-mediated target-directed polymerization, or when taken together form 2'-3'-didehydroribose.

38. The labelled nucleoside or nucleotide of claim 33 which is enzymatically extendable.

39. A labelled polynucleotide comprising a polynucleotide covalently attached to a label, wherein the label is a substantially pure atropisomer of a xanthene compound having the structure;

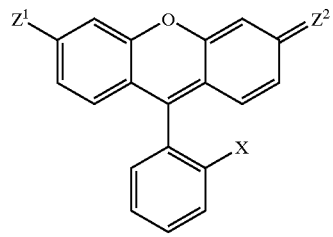

wherein $Z^1$ is OH, $NH_2$, NHR, or $NR_2$, wherein each R is independently hydrogen, $C_1$–$C_{12}$ alkyl, phenyl, benzyl, aryl, heterocycle, or a linking moiety;

$Z^2$ is O, $^+NH_2$, $^+NHR$, or $^+NR_2$, wherein each R is independently hydrogen, $C_1$–$C_{12}$ alkyl, phenyl, benzyl, aryl, heterocycle, or a linking moiety;

X is carboxylate or sulfonate, and said structure includes aryl-substituted forms thereof.

40. The labelled polynucleotide of claim 39 comprising the formula:

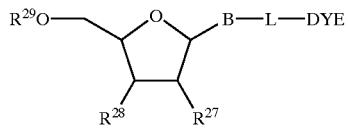

wherein

DYE is a substantially pure atropisomer of a xanthene compound;

B is a nucleobase;

L is a linker;

$R^{27}$ is H, OH, halide, azide, amine, alkylamine, $C_1$–$C_6$ alkyl, allyl, $C_1$–$C_6$ alkoxy, $OCH_3$, or $OCH_2CH\!=\!CH_2$; and $R^{28}$ and $R^{29}$ when taken alone, are each independently H, phosphate, internucleotide phosphodiester, or internucleotide analog;

wherein the polynucleotide comprises 2 to 100 nucleotides.

41. The labelled polynucleotide of claim 40 wherein B is selected from the group consisting of uracil, thymine, cytosine, adenine, 7-deazaadenine, guanine, and 7-deazaguanosine.

42. The labelled polynucleotide of claim 39 comprising the formula:

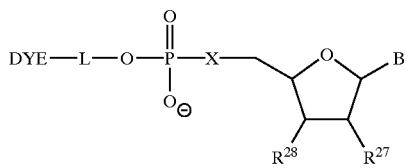

wherein

DYE is a substantially pure atropiscmer of a xanthene compound;

B is a nucleobase;

X is O, NH, or S;

L is a linker;

$R^{27}$ is H, OH, halide, azide, amine, alkylamine, $C_1$–$C_6$ alkyl, allyl, $C_1$–$C_6$ alkoxy, $OCH_3$, or $OCH_2CH=CH_2$; and $R^{28}$ is internucleotide phosphodiester or internucleotide analog;

wherein the polynucleotide comprises 2 to 100 nucleotides.

43. The labelled polynucleotide of claim 42 wherein B is selected from the group consisting of uracil, thymine, cytosine, adenine, 7-deazaadenine, guanine, and 7-deazaguanosine.

44. The labelled polynucleotide of claim 42 in which L is $C_1$–$C_{12}$ alkyldiyl.

45. The labelled polynucleotide of claim 42 in which L comprises $—(CH_2CH_2O)_n—$, where n is 1 to 100.

46. A labelled polypeptide comprising a polypeptide covalently attached to a substantially pure atropisomer of a xanthene compound having the structure:

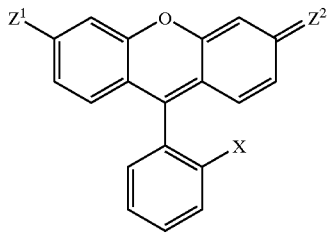

wherein $Z^1$ is OH, $NH_2$, NHR, or $NR_2$, wherein each R is independently hydrogen, $C_1$–$C_{12}$ alkyl, phenyl, benzyl, aryl, heterocycle, or a linking moiety;

X is carboxylate or sulfonate, and said structure includes aryl-substituted forms thereof.

47. A phosphoramidite compound having the formula:

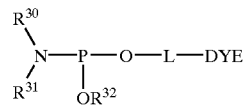

wherein DYE is a substantially pure atropisomer of a xanthene compound having the structure:

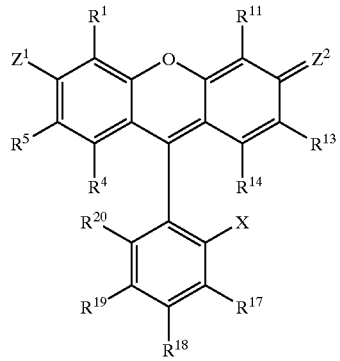

wherein $Z^1$ is OH, $NH_2$, NHR, or $NR_2$, wherein each R is independently hydrogen, $C_1$–$C_{12}$ alkyl, phenyl, benzyl, aryl, heterocycle, or a linking moiety;

$Z^2$, is O, $^+NH_2$, $^+NHR$, or $^+NR_2$, wherein each R is independently hydrogen, $C_1$–$C_{12}$ alkyl, phenyl, benzyl, aryl, heterocycle, or a linking moiety;

X is carboxylate or sulfonate,

L is a linker;

$R^{30}$ and $R^{31}$ taken separately are selected from the group consisting of $C_1$–$C_{12}$ alkyl, $C_1$–$C_{12}$ cycloalkyl, and aryl; or $R^{30}$ and $R^{31}$ taken together with the nitrogen atom form a saturated nitrogen heterocycle; and $R^{32}$ is a phosphite ester protecting group; and wherein DYE is optionally aryl-substituted.

48. The phosphoramidite compound of claim 47 wherein $R^{32}$ is selected from the group consisting of methyl, 2-cyanoethyl, and 2-(4-nitrophenyl)ethyl.

49. The phosphoramidite compound of claim 47 wherein $R^{30}$ and $R^{31}$ are each isopropyl.

50. The phosphoramidite compound of claim 47 wherein $R^{30}$ and $R^{31}$ taken together is morpholino.

51. The phosphoramidite compound of claim 47 wherein L is $C_1$–$C_{12}$ alkyidyl.

52. The phosphoramidite compound of claim 47 wherein L is attached at $R^{18}$ or $R^{19}$ of DYE having the structure:

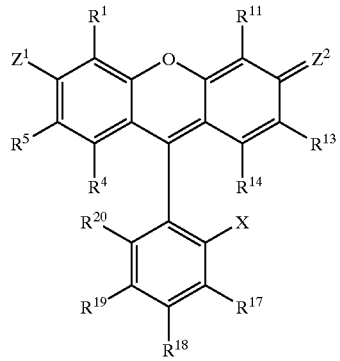

53. The phosphoramidite compound of claim 52 having the structure:

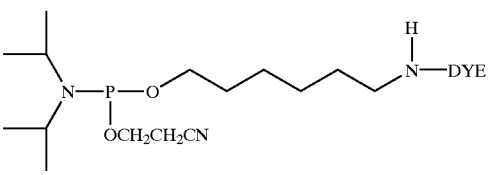

54. The phosphoramidite compound of claim 47 wherein L is

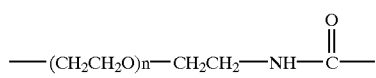

and n ranges from 1 to 10.

55. A kit for generating a labelled primer extension product, comprising one or more enzymatically-incorporatable nucleotides and a primer, wherein at least one nucleotide is a labelled nucleotide according to claim 52.

56. The kit of claim 55 wherein the labelled nucleotide is a terminator.

57. The kit of claim 56 which comprises four different terminators, one which terminates at a target A, one which terminates at a target G, one which terminates at a target C and one which terminates at a target T or U.

* * * * *